US007658763B2

(12) United States Patent
Stobie

(10) Patent No.: US 7,658,763 B2
(45) Date of Patent: *Feb. 9, 2010

(54) HEART VALVE HOLDER AND METHOD FOR RESISTING SUTURE LOOPING

(75) Inventor: Robert Stobie, Mission Viejo, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 514 days.

This patent is subject to a terminal disclaimer.

(21) Appl. No.: 11/181,491

(22) Filed: Jul. 13, 2005

(65) Prior Publication Data

US 2005/0251252 A1 Nov. 10, 2005

Related U.S. Application Data

(63) Continuation of application No. 10/705,587, filed on Nov. 10, 2003, now Pat. No. 6,966,925, which is a continuation of application No. 09/745,386, filed on Dec. 21, 2000, now Pat. No. 6,964,682.

(51) Int. Cl.
*A61F 2/24* (2006.01)
(52) U.S. Cl. .................................................. 623/2.11
(58) Field of Classification Search .......... 623/2.1–2.42
See application file for complete search history.

(56) References Cited

U.S. PATENT DOCUMENTS

| 3,409,013 | A | | 11/1968 | Barry | |
|---|---|---|---|---|---|
| 3,628,535 | A | | 12/1971 | Ostrowsky et al. | |
| 4,702,250 | A | | 10/1987 | Ovil et al. | |
| 4,865,600 | A | * | 9/1989 | Carpentier et al. | 623/2.11 |
| 5,443,502 | A | * | 8/1995 | Caudillo et al. | 623/2.11 |
| 5,476,510 | A | * | 12/1995 | Eberhardt et al. | 623/2.11 |
| 5,531,785 | A | * | 7/1996 | Love et al. | 623/2.11 |
| 5,728,153 | A | * | 3/1998 | Menkis et al. | 606/139 |
| 5,776,187 | A | * | 7/1998 | Krueger et al. | 623/2.11 |
| 5,824,068 | A | | 10/1998 | Bugge | |
| 5,861,028 | A | * | 1/1999 | Angell | 623/2.11 |
| 6,126,007 | A | | 10/2000 | Kari et al. | |
| 6,197,053 | B1 | | 3/2001 | Cosgrove et al. | |
| 6,214,043 | B1 | | 4/2001 | Krueger et al. | |
| 6,409,758 | B2 | * | 6/2002 | Stobie et al. | 623/2.11 |
| 6,702,852 | B2 | * | 3/2004 | Stobie et al. | 623/2.11 |

(Continued)

FOREIGN PATENT DOCUMENTS

WO    WO-97/25004 A1    7/1997

*Primary Examiner*—Alvin J Stewart
(74) *Attorney, Agent, or Firm*—Rajiv Yadav, Esq.; Guy Cumberbatch, Esq.

(57) ABSTRACT

An improved holder and method for implanting a tissue-type prosthetic mitral heart valve that prevents suture looping and ma y also constrict the commissure posts of the valve. An upstanding or shaft member axially positioned on the holder causes the lengths of attachment sutures to extend axially beyond the commissure post tips to create a tent and prevent looping of any of an array of pre-implanted sutures around the tips during deployment of the valve. The shaft member may be axially movable such that it can be initially retracted and then actuated just prior to valve deployment. The shaft member may have notches on its distal tip for capturing the attachment sutures, which are crossed over along the valve axis to ensure engagement by the notches. The attachment sutures may be strands or filaments, or may be wider bands of flexible biocompatible material. If bands are used, they desirably cover the commissure post tips to further help prevent suture looping thereover. The flexible lengths of material extend directly between commissures of the valve, or may extending radially inward from each commissure to a central upstanding member.

22 Claims, 14 Drawing Sheets

U.S. PATENT DOCUMENTS

| | | |
|---|---|---|
| 6,802,860 B2 | 10/2004 | Cosgrove et al. |
| 6,964,682 B2 * | 11/2005 | Nguyen-Thien-Nhon et al. .................... 623/2.11 |
| 6,966,925 B2 * | 11/2005 | Stobie ..................... 623/2.11 |
| 7,189,258 B2 * | 3/2007 | Johnson et al. ............ 623/2.11 |
| 7,468,073 B2 * | 12/2008 | Johnson et al. ............ 623/2.11 |
| 7,503,929 B2 * | 3/2009 | Johnson et al. ............ 623/2.11 |
| 2002/0082686 A1 | 6/2002 | Nguyen-Thien-Nhon et al. |
| 2003/0023303 A1 * | 1/2003 | Palmaz et al. .............. 623/2.18 |
| 2003/0125805 A1 * | 7/2003 | Johnson et al. ............ 623/2.11 |
| 2004/0024451 A1 * | 2/2004 | Johnson et al. ............ 623/2.11 |
| 2004/0138741 A1 * | 7/2004 | Stobie et al. ............... 623/2.11 |

* cited by examiner

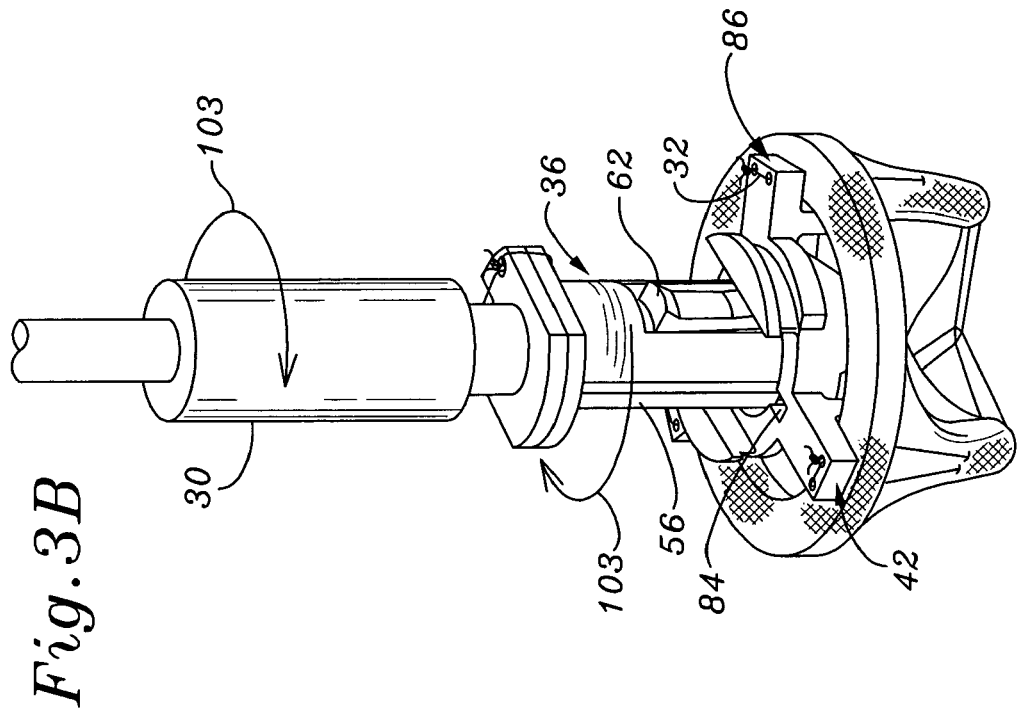
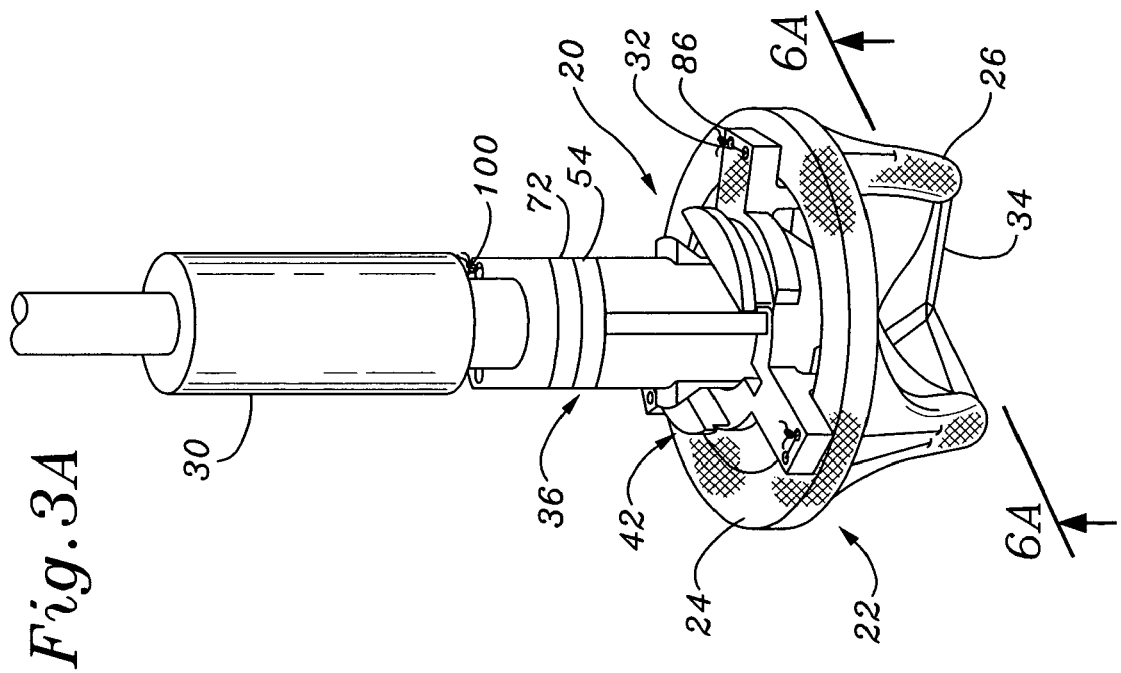

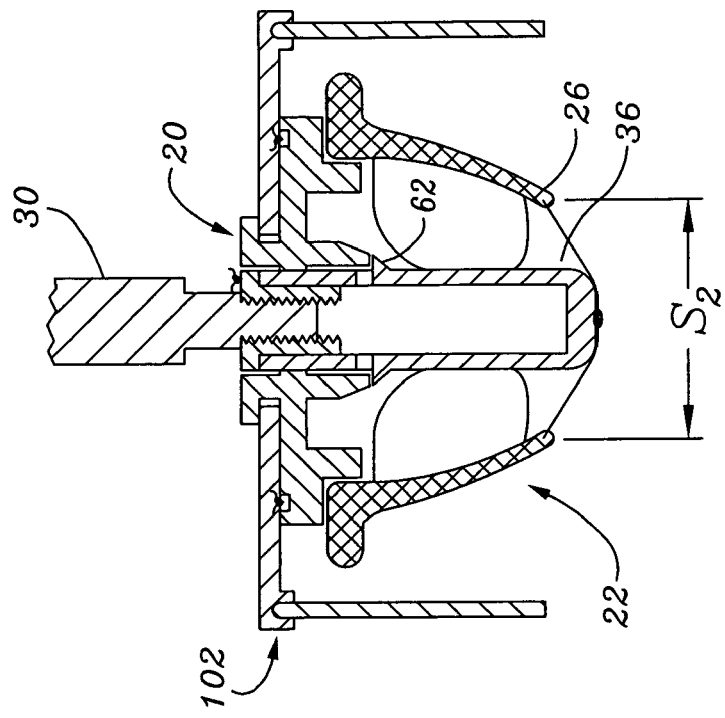
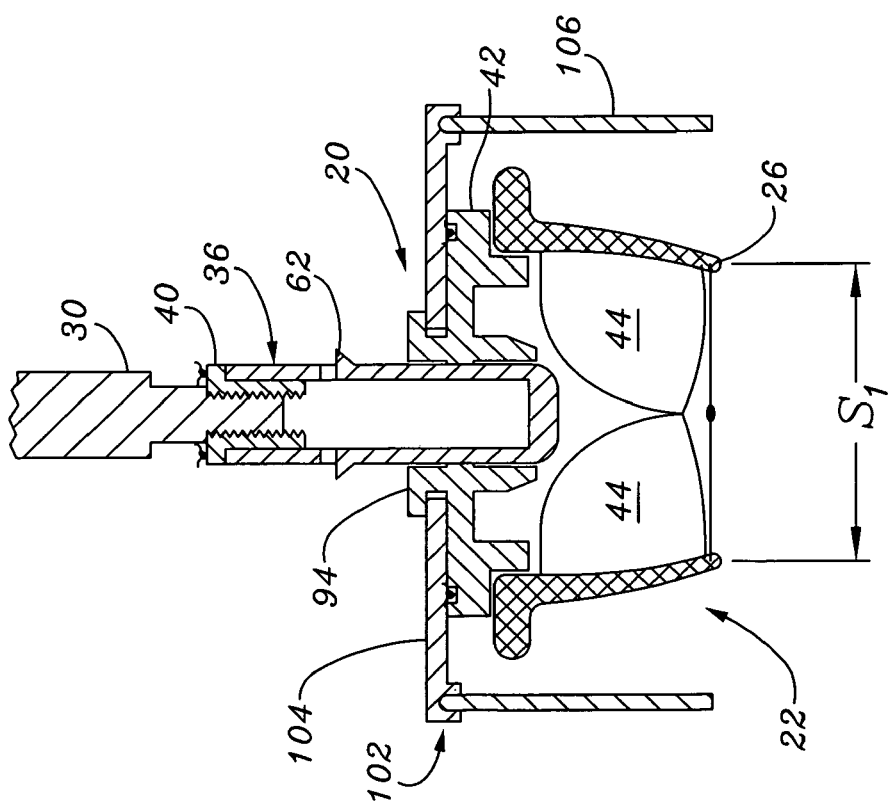
Fig. 4B
Fig. 4A

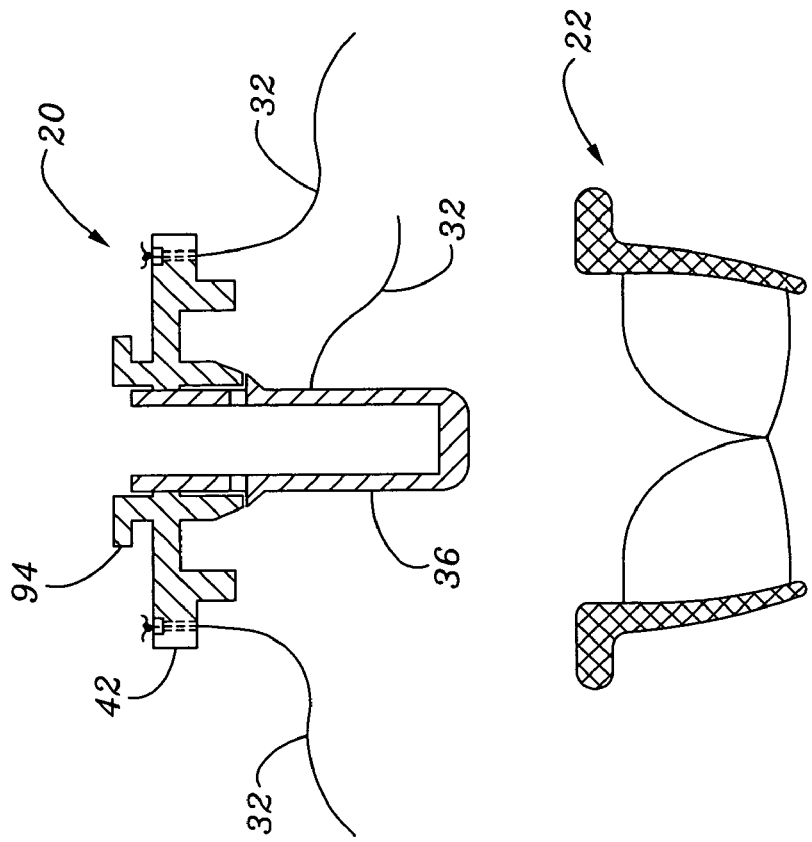
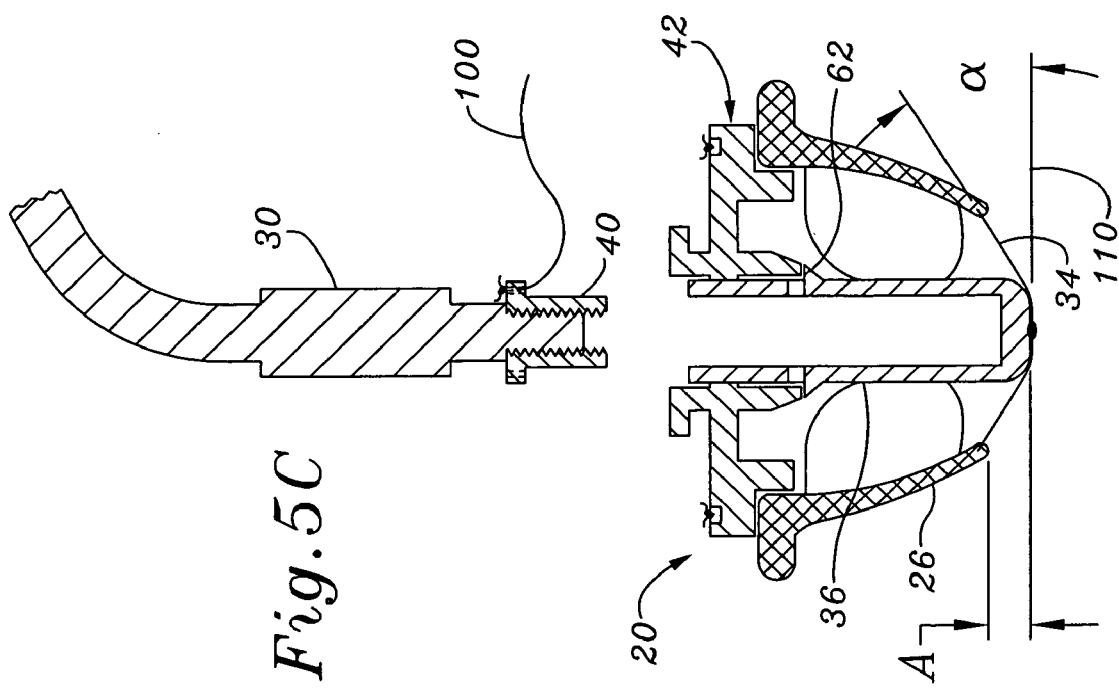

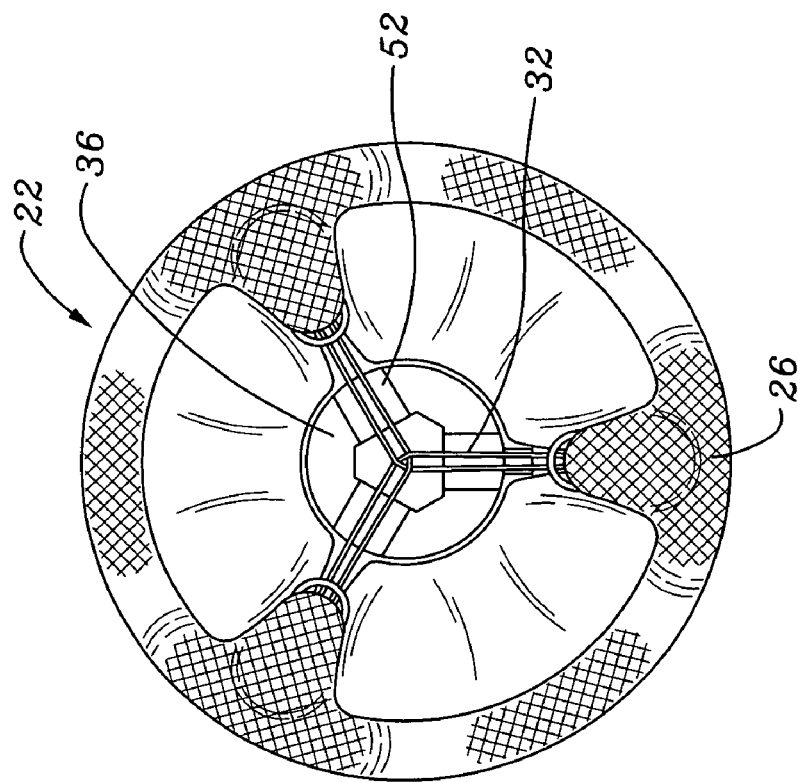
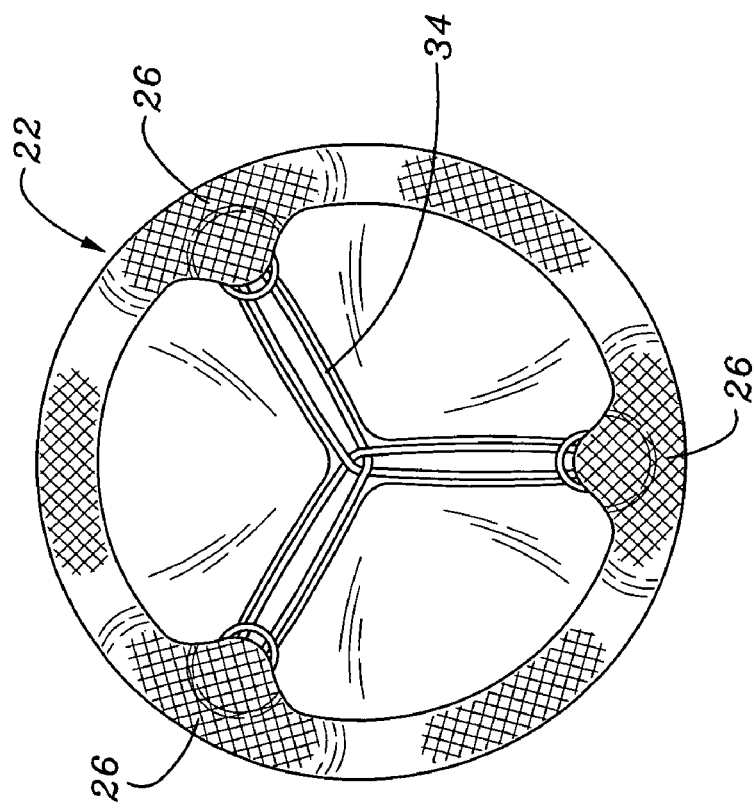

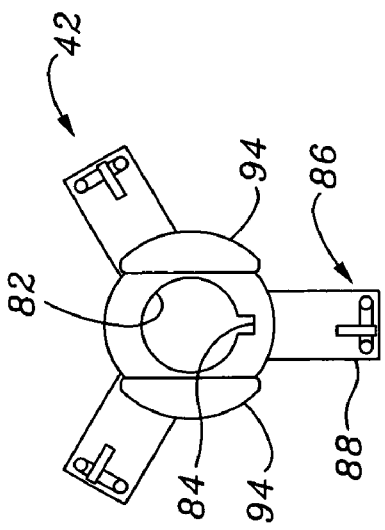
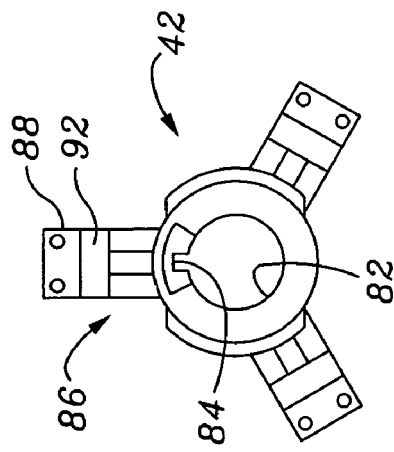
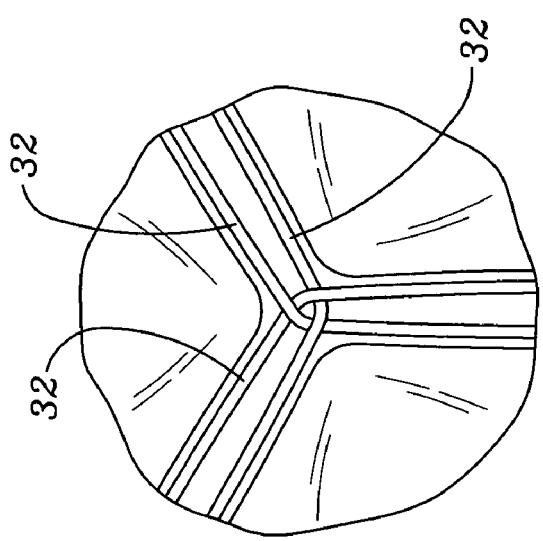

HEART VALVE HOLDER AND METHOD FOR RESISTING SUTURE LOOPING

RELATED APPLICATIONS

The present application is a continuation of U.S. application Ser. No. 10/705,587, filed Nov. 10, 2003, now U.S. Pat. No. 6,966,925, entitled "HEART VALVE HOLDER AND METHOD FOR RESISTING SUTURE LOOPING," which is a continuation of U.S. application Ser. No. 09/745,386, filed Dec. 21, 2000, now U.S. Pat. No. 6,964,682, entitled "HEART VALVE HOLDER THAT RESISTS SUTURE LOOPING," the disclosures of which are expressly incorporated by reference herein.

FIELD OF THE INVENTION

The present invention relates generally to medical devices, and more particularly to a holder that facilitates the implantation of a bioprosthetic replacement heart valve, particularly a mitral valve, and associated methodology.

BACKGROUND OF THE INVENTION

In mammalian animals, the heart is a hollow muscular organ having four pumping chambers: the left and right atria and the left and right ventricles, each provided with its own one-way valve. The natural heart valves are identified as the aortic, mitral (or bicuspid), tricuspid and pulmonary valves, and each has leaflets to control the directional flow of blood through the heart. The valves are each supported by an annulus that comprises a dense fibrous ring attached either directly or indirectly to the atrial or ventricular muscle fibers. Various surgical techniques may be used to repair a diseased or damaged valve. In a valve replacement operation, the damaged leaflets are excised and the annulus sculpted to receive a replacement valve.

Two primary types of heart valve replacements or prostheses are known. One is a mechanical-type heart valve that uses a ball and cage arrangement or a pivoting mechanical closure to provide unidirectional blood flow. The other is a tissue-type or "bioprosthetic" valve which is typically constructed with natural-tissue valve leaflets that function much like a natural human heart valve's, imitating the natural action of the leaflets to coapt against each other and ensure the one-way blood flow. In tissue valves, a whole xenograft valve (e.g., porcine) or a plurality of xenograft leaflets (e.g., bovine pericardium) provide occluding surfaces that are mounted within a surrounding stent structure. Research is ongoing on synthesizing the tissue leaflets, and therefore the term "flexible leaflet valve" refers to both natural and artificial "tissue-type" valves. In both types of prosthetic valves, a biocompatible cloth-covered suture or sewing ring is provided, on the valve body for the mechanical type of prosthetic valve, or on the inflow end of the stent for the tissue-type of prosthetic valve.

When placing a tissue type prosthetic valve in the mitral position, the commissure posts are on the blind side of the valve and may become entangled with pre-installed sutures, potentially damaging the annulus or tissue during delivery. The difficulty of the delivery task is compounded if the surgery is through a minimally-invasive access channel, a technique that is becoming more common. The problem of entanglement is termed "suture looping," and means that the suture that is used to attach or mount the valve to the heart tissue is inadvertently wrapped around the inside of one or more of the commissure post tips. If this occurs, the looped suture may damage one of the tissue leaflets when tightly tied down, or at least may interfere with the implant procedure or valve operation and prevent maximum coaptation of the valve leaflets, resulting in a deficiency in the prosthetic mitral valve.

Some attempts have been made to overcome these problems in current holders for prosthetic mitral valves. An example of such a holder is U.S. Pat. No. 4,865,600, Carpentier, et al., incorporated herein by reference. Carpentier provides a holder having a mechanism that constricts the commissure posts inwardly prior to implantation. The Carpentier device provides an elongate handle to both hold the valve/valve holder combination during implantation, as well as to cause the commissure posts to constrict inwardly. The valve is connected to the valve holder by the manufacturer using one or more sutures, and the combination shipped and stored as a unit. During the valve replacement procedure, the surgeon connects the handle to the holder and locks a locking nut to hold the commissure posts at a given constricted position. The surgeon then attaches the sewing ring of the valve to the native valve annulus with an array of sutures that has been pre-embedded in the annulus and extended outside the body. The valve is then advanced along the array of sutures to its desired implantation position and the sutures tied off. When the holder is cut free, the commissure posts are released to expand and the holder may be removed using the handle. However, even when the commissure posts are constricted, slack in the array of sutures, for example, may lead to looping of sutures around one of the cloth-covered commissure posts, which interferes with the implantation procedure.

What is needed then is an improved tissue-type prosthetic valve holder attachable to the inflow end of the valve that insures against suture looping.

SUMMARY OF THE INVENTION

The present invention provides a holder for a tissue-type prosthetic heart valve having an inflow end and an outflow end and a flow axis therebetween. The valve includes an annular sewing ring at the inflow end attached to a stent having posts circumferentially-spaced about the flow axis that support occluding tissue surfaces of the valve. In this type of valve the posts are cantilevered generally in the outflow direction.

The present invention provides an improved holder system for preventing suture looping around the commissure posts of tissue-type heart valves that are implanted in the direction where the commissure posts form the leading end of the valve. For instance, the present invention provides an improved holder for a mitral valve where lengths of flexible material connect the holder and valve and extend between the commissure posts of the valve. Each length of flexible material extends axially, desirably through the valve, to be connected at two points to a rigid holder structure that abuts the inflow end of the valve. Severing the lengths of flexible material near one of the attachment points permits removal of the entire length of material from the valve along with the rigid structure, by virtue of the second attachment point. In a preferred embodiment, the rigid structure incorporates a mechanism for tensioning the lengths of flexible material to cause the commissure posts of the valve to flex inward.

In accordance with one aspect the present invention, a holder for a flexible leaflet prosthetic heart valve is provided. The heart valve is attachable to a surgical delivery handle and has an inflow end, an outflow end, and a flow axis therebetween. The heart valve is of the type that includes an annular sewing ring at its inflow end and a plurality of generally axially-extending commissure posts circumferentially-spaced around the outflow end that support occluding flexible leaflets of the valve. The holder includes a rigid valve abutment portion, a shaft member, and a plurality of lengths of flexible material. The valve abutment portion contacts the annular sewing ring at the inflow end of the valve. The shaft member is axially movable relative to the valve abutment portion between a first position wherein a distal tip of the shaft member is located to the inflow side of the leaflets, and a second position wherein the distal tip is located to the outflow side of the leaflets. The lengths of flexible material extend in a taut fashion across the outflow end of the valve to prevent suture looping, and each length of flexible material has first segments extending radially inward from the commissure posts to the shaft member in its second position. Desirably, the commissure tips of the valve are flexible and extend generally axially in the first position of the shaft member but are cantilevered radially inward by engagement of the shaft member with the lengths of flexible material in the second position of the shaft member. Furthermore, the lengths of flexible material may be secured to the valve abutment portion at both ends.

In accordance with one embodiment, the distal tip of the shaft member in its second position extends axially beyond the commissure posts such that each first segment of the lengths of flexible material extends at an angle both radially inward and axially in the outflow direction to the distal tip of the shaft member. Preferably, the shaft member includes notches on its distal tip for receiving midpoints of the first segments of the lengths of flexible material. Each first segment therefore extends from one of the commissure posts radially inward to the shaft member and then radially outward to an adjacent commissure post via a notch in the shaft member.

Desirably, the valve abutment portion comprises a tubular body having a bore for receiving the shaft member, shaft member being axially movable within the bore between the first and second positions. The holder may further include structure for axially restraining the shaft member in the second position with respect to the valve abutment portion. For example, a cantilevered pawl on the shaft member may be provided that engages the bore of the valve abutment portion and axially restrains the shaft member in the second position. Also, structure may be provided for rotationally restraining the shaft member with respect to the valve abutment portion as the shaft member moves between the first and second positions.

The present invention also provides a holder for a tri-leaflet flexible leaflet prosthetic heart valve as described above. The holder includes a shaft member that is axially movable relative to the valve along its flow axis between a first position and a second position, the shaft member having a distal tip. Three lengths of flexible material extend in a taut fashion across the outflow end of the valve to prevent suture looping, and each length of flexible material has a first segment that extends radially inward and mutually crosses over the other two first segments so that each remains along the flow axis of the valve. With this arrangement, the distal tip of the shaft member contacts the crossed-over first segments in its second position and displaces them to be angled in the outflow direction.

The tri-leaflet valve holder may also include a valve abutment portion in contact with the valve sewing ring to which each length of flexible material is secured at both ends. The valve abutment portion may have outwardly extending brackets for engaging the valve sewing ring, the brackets having through holes for receiving and securing the lengths of flexible material. Preferably, the valve abutment portion comprises a tubular body having a bore for receiving the shaft member, which is axially movable therein between the first and second positions. The holder may include structure for axially restraining the shaft member in the second position with respect to the valve abutment portion, such as a cantilevered pawl on the shaft member that engages the bore of the valve abutment portion. Further, the holder may have structure for rotationally restraining the shaft member with respect to the valve abutment portion as the shaft member moves between the first and second positions. The holder may also include a handle interface releasably secured with sutures to the shaft member and having a threaded bore for receiving an externally threaded boss on a distal end of a surgical delivery handle. The handle interface and delivery handle can be disengaged from the shaft member upon severing the sutures. Desirably, the shaft member includes notches on its distal tip for capturing and retaining the first segments of the lengths of flexible material.

In one particular embodiment, a holder is provided that includes a plurality of lengths of flexible material extending in a taut fashion across the outflow end of the valve to prevent suture looping, each length of material having a first segment extending directly between adjacent commissure posts and crossing over each adjacent length of material adjacent to the commissure post. The lengths of flexible material may be sutures, or may comprise a band of biocompatible material, such as polyester. In the latter instance, the band of material may completely cover each commissure post, and may cross over adjacent bands of material. Desirably, a slide is created by the lengths of flexible material adjacent each commissure post, for example by crossing over suture filaments at or radially inward from the commissure posts.

In another embodiment of the invention, the holder includes a plurality of lengths of flexible material extending in a taut fashion across the outflow end of the valve to prevent suture looping, each length of material having a first segment extending in a band that a substantially wider than it is thick directly between adjacent commissure posts. Each length of flexible material may extend in second segments along two adjacent commissure posts to be attached to the rigid structure at two points. Desirably, the commissure posts are cloth covered and the second segments pass beneath the cloth covering in a configuration that is not as wide as the first segments.

In a further aspect of the present invention, the holder includes a central upstanding member passing along the axis of the valve from the inflow side to the outflow side of the leaflets. A plurality of lengths of flexible material extend in a taut fashion across the outflow end of the valve to prevent suture looping, each length of flexible material having first segments extending radially inward from one of the commissure posts, preferably at a steep angle, to the central upstanding member. The central upstanding member may be hollow, with each length of flexible material passing into and through the member.

Alternatively, the upstanding member may be solid and include notches for capturing and retaining the midpoints of the first segments of lengths of flexible material. In this case, each first segment extends, preferably at a steep angle, from one of the commissure posts radially inward to the upstanding member and then radially outward to an adjacent commissure post via a notch. The upstanding member may include a wide base on an end that is attached to a rigid structure of the holder that abuts the sewing ring. A narrow shaft extends from the wide base and passes between and to the outflow side of the leaflets. The narrow shaft may have a non-circular cross-section, such as triangular, to reduce deformation of the leaflets from long-term storage.

The holder may include a valve abutment portion sized and shaped to abut the sewing ring at the inflow end of the valve. The holder may further include a commissure post constriction mechanism adapted to constrict the commissure posts radially inward from a relaxed position to a constricted position when actuated by a handle. A retaining mechanism may also be provided that retains the commissure post constriction mechanism in the constricted position after the handle is removed.

In one embodiment the commissure post constriction mechanism comprises an adjusting portion and an adjusting member adapted to adjust the distance between the adjusting portion and the valve abutment portion, and one or more filaments attached to the adjusting portion and sutured through the end of the commissure posts distal to the adjusting portion. When the adjusting member is operated to separate the adjusting portion from the valve abutment portion the adjusting portion pulls the filaments, which in turn urge the end of the commissure posts distal to the adjusting portion radially inwardly, to the constricted position.

The valve abutment portion may have a planar shape, with the adjusting portion having a substantially complementary planar shape. It is preferred that the planar shape of the valve abutment portion be comprised of a plurality of tangs radiating from a central body to each cover a portion of the sewing ring. In this manner a sufficient amount of the sewing ring is left exposed to allow for suturing the sewing ring to the native annulus. Stated another way, the holder may include two relatively movable plates, one of which attaches to the valve sewing ring on the inflow end of the valve and the other which attaches via sutures or similar expedient to the valve commissures on the outflow end. Separation of the plates places the sutures in tension and constricts the commissures.

Adjustment of the distance between the valve abutment portion and the adjusting portion (e.g., relatively movable plates) may be achieved by providing a central threaded aperture in the adjusting portion and an adjusting member that cooperates with this threaded aperture. In this construction the end of the adjusting member proximal the valve abutment portion abuts the valve abutment portion during operation. When the adjusting member is advanced through the central aperture of the adjusting portion it pushes the valve abutment portion and the two portions separate.

A handle may be operatively connected to the adjusting member to turn it by providing a handle that has an externally threaded end portion and an adjusting member having a central longitudinal threaded bore sized to receive the threaded end portion. When the handle is introduced into the bore it is rotated in a first direction and will seat in the threaded bore of the adjusting member. Further rotation of the adjusting member separates the adjusting portion from the valve abutment portion, as recited above, and causes the commissure posts to constrict inwardly.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

FIG. 3A is a perspective view of an assembled heart valve holder of FIG. 2 attached to a heart valve and a surgical handle;

FIG. 3B is a perspective view as in FIG. 3A after rotation of the surgical handle and a shaft member of the holder relative to a valve abutment portion and prior to actuation of the shaft member;

FIG. 4A is an axial sectional view of the assembled holder of FIG. 2 and heart valve with the shaft member in its first position, and also showing a protective transport cage;

FIG. 4B is a sectional view like FIG. 4A and corresponding to the second position of the shaft member shown in FIG. 3C;

FIG. 5C is an axial sectional view of the holder, handle and valve combination and showing the rapid detachment of the handle along with the handle interface;

FIG. 5D is an axial sectional view of the holder after having been detached from the valve;

FIG. 6A is an outflow plan view of the assembled holder and valve as seen along line 6A-6A in FIG. 3A prior to actuation of the shaft member and simultaneous constriction of valve commissure tips;

FIG. 6B is an outflow plan view of the assembled holder and valve as seen along line 6B-6B in FIG. 3C after actuation of the shaft member and constriction of the valve commissure tips;

FIG. 7 is an enlarged plan view taken within the circle indicated in FIG. 6A along the valve flow axis illustrating the cross over of a plurality of lengths of flexible material securing the holder to the valve;

FIGS. 8 and 9 are opposite plan views of a valve abutment portion of the exemplary holder of FIG. 2.

DESCRIPTION OF THE PREFERRED EMBODIMENTS

The present invention provides an improved heart valve holder for tissue-type prosthetic heart valves that facilitates implantation and reduces the chance of suture entanglement. The holder of the present invention is particularly useful for prosthetic mitral heart valves having commissure posts on the outflow side supporting flexible leaflets therebetween. The mitral position is such that the outflow side (and commissure posts) projects distally toward the left ventricle during implantation, and thus the holder must be attached to the inflow (i.e., accessible) side of the valve. Delivery of the valve to the mitral position involves sliding the valve down a plurality or array of sutures that have been pre-installed around the annulus and then passed through the valve sewing ring. The holder of the present invention constricts the commissure posts radially inward and at the same time moves the flexible material upwards to form a steep angle thus helping to prevent the leading posts from becoming entangled in the array of pre-installed sutures. This benefit is thus especially advantageous where the outflow side and commissure posts of the heart valve extend distally during delivery, forming the leading end of the valve, which is the case in a prosthetic mitral valve implantation. Nonetheless, the holder of the present invention may prove useful for the implantation of heart valves in other than the mitral position, and thus the invention may be applicable thereto.

Figure 1A:
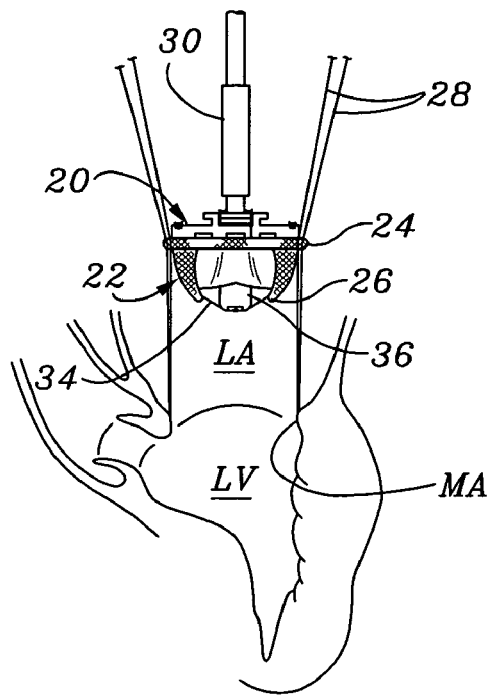
FIGS. 1A-1C are schematic elevational views of the deployment of a prosthetic heart valve using an exemplary holder of the present invention.

FIGS. 1A-LC illustrates several steps in an exemplary heart valve deployment process using a holder 20 of the present invention. The holder 20 is shown assembled to a flexible leaflet heart valve 22 having a sewing ring 24 and a plurality of commissure posts 26 that support leaflets of a tissue valve or a plurality of separate flexible leaflets. This particular valve 22 is intended for implant in the mitral annulus MA, between the left atrium LA and left ventricle LV. Blood flows from the left atrium LA along a flow axis through the valve 22 and into the left ventricle LV during the heart's diastolic phase, and therefore the commissure posts 26 project in an outflow direction.

FIG. 1A illustrates a plurality of implant sutures 28 that have been pre-threaded through the periphery of the mitral annulus MA and then through the sewing ring 24 of the valve 22. In the typical procedure, an array of implant sutures 28 is pre-threaded around the periphery of the mitral annulus MA and loose ends are removed from the surgical site to be threaded through the sewing ring 24 outside of the body. The valve 22 is then "parachuted" down the array of sutures until it rests on the annulus. A surgical handle 30 removably attaches to the holder 20 and facilitates manipulation and advancement of the holder/valve combination down the array of implant sutures 28.

As will be more clear from the later drawings and description, the holder 20 removably attaches to the valve 22 using a plurality of lengths of flexible material 32, first segments 34 of which are visible in FIG. 1A at the outflow end of the valve 22. The holder 20 further includes an upstanding or shaft member 36 that extends along the flow axis of the valve and displaces the first segments 34 into the tent configuration shown. The first segments 34 extend radially inward from the outflow end of commissure posts 26 to the flow axis. Tension in the first segments 34 pulls the commissure posts 26 inward and also moves the first segments 34 upwards to form a steep angle, thus helping to prevent entanglement of any of the commissure posts with the array of implant sutures 28.

Figure 1B:
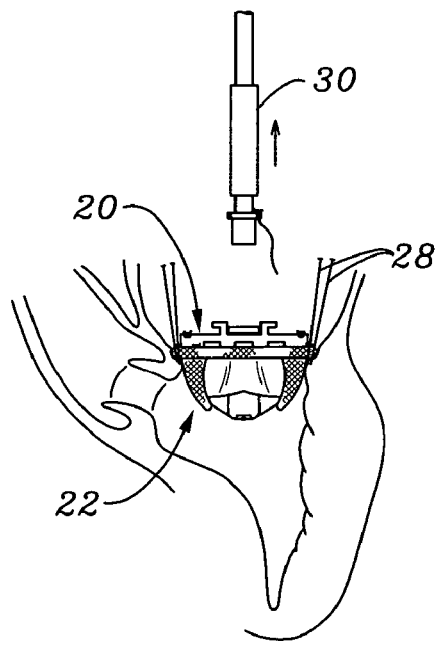

FIG. 1B shows the holder 20 and valve 22 combination assembled with the sewing ring 24 seated on the mitral annulus MA. The surgical handle 30 detaches from the holder 20 by unscrewing or, preferably, along with a handle interface of the holder by severing a flexible thread, as will be described below.

Figure 1C:
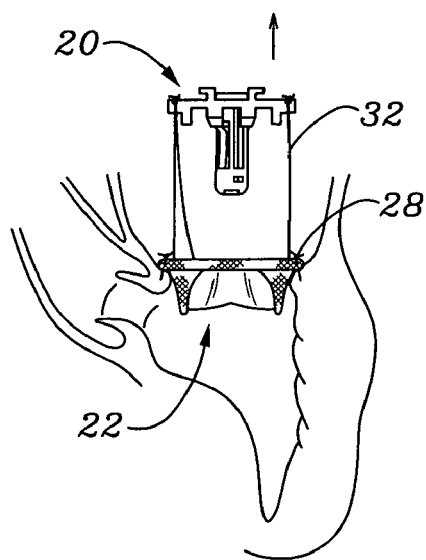

Once the handle 30, preferably along with the handle interface 40, is removed to provide greater visibility, the surgeon ties off the implant sutures 28 and severs them close to the sewing ring 24 to secure the valve 22 in the annulus, as seen in FIG. 1C. The surgeon then detaches the holder 20 from the valve 22 by severing each of the lengths of flexible material 32. Each length of flexible material 32 is tied to the holder at both ends, and severing it in the middle, at a cutting groove in the holder, permits the holder with the lengths of flexible material attached, to be pulled free of the valve 22.

Figure 2:
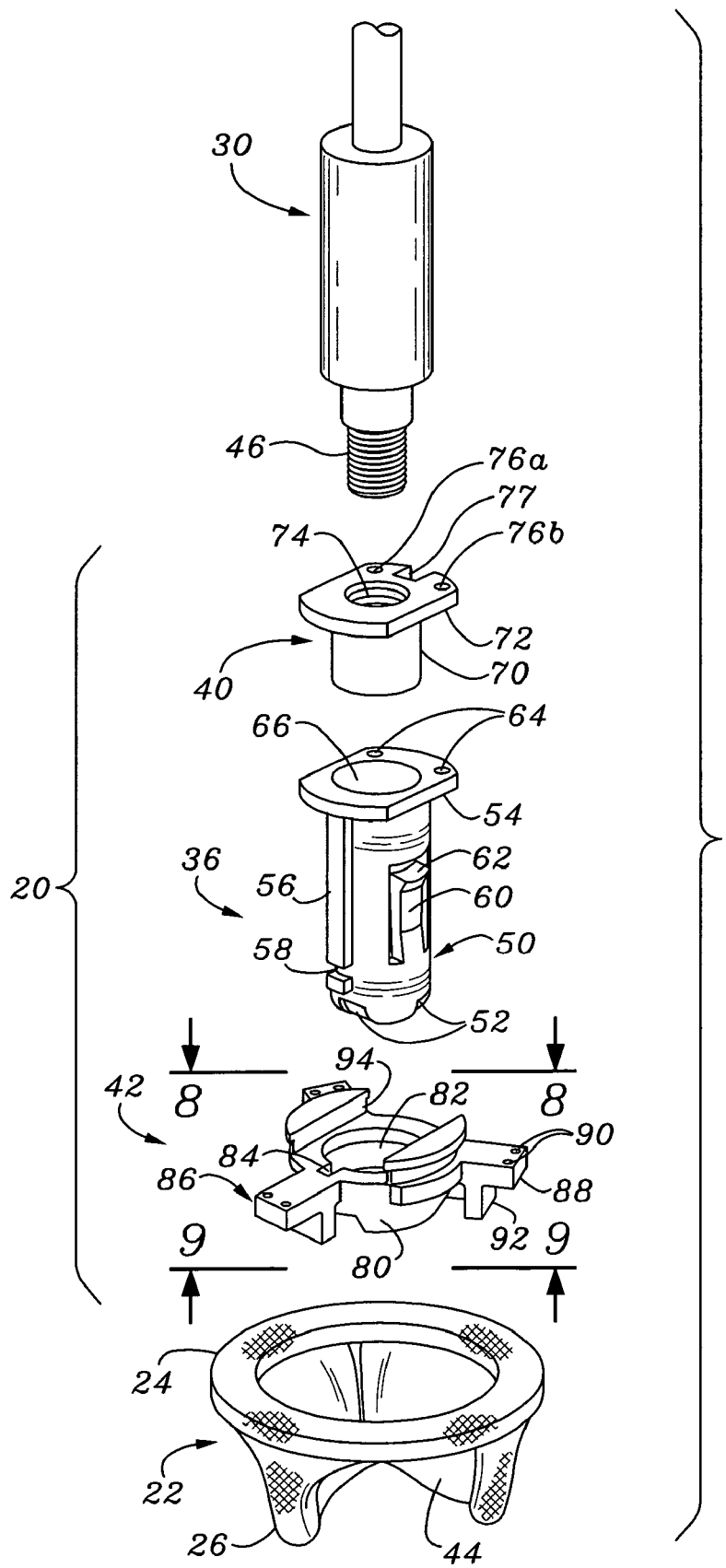
FIG. 2 is an exploded perspective view of an exemplary heart valve holder of the present invention along with a representative heart valve and surgical handle.

With reference to FIG. 2, the components of an exemplary holder 20 are shown exploded along with the prosthetic heart valve 22 and handle 30. The holder 20 comprises the aforementioned shaft member 36, a handle interface 40, and a valve abutment portion 42. Prior to a detailed discussion of these components, it will be seen that the heart valve 22 includes a generally annular sewing ring 24 on an inflow end and a plurality of commissure posts 26 on an outflow end. Flexible leaflets 44 provide occluding surfaces for the valve 22 and are supported by the commissure posts 26. Various flexible leaflet prosthetic heart valves are known and would benefit from deployment using the holder 20 of the present invention. Exemplary heart valves are the CARPENTIER-EDWARDS porcine and pericardial bioprostheses, sold by Edwards Lifesciences Corp. of Irvine, Calif. The surgical handle 30 is of a conventional type and includes a threaded boss 46 on its distal end.

The lengths of flexible material 32, typically suture material, which couple the holder 20 to the valve 22 are not illustrated in FIG. 2. More detailed discussions of the attachment of a holder to a heart valve using such suture material, and structure on the holder permitting rapid detachment, can be found in U.S. Pat. Nos. 4,865,600 and 6,409,758, both of which are expressly incorporated herein by reference.

With reference still to FIG. 2, the shaft member 36 possesses a generally tubular body 50 having notches 52 on a distal end and an outwardly extending flange 54 on a proximal end (in this sense, proximal corresponds to the inflow side of the valve 22 and distal to the outflow side). On one lateral side of the tubular body 50, a rail 56 extends axially from the flange 54 into proximity with the distal end, and is interrupted by a small gap 58. One or more cantilevered fingers 60 having outwardly projecting pawls 62 are formed in the tubular body 50. Each of the pawls 62 is on the proximal end of the respective finger 60. In a preferred embodiment, there are at least two such fingers 60 and pawls 62. The flange 54 includes at least one, and preferably at least two coupling holes 64 whose purpose will be explained below. The shaft member 36 further defines a bore or cavity 66 opening to its proximal end, the distal end being closed in the illustrated embodiment.

The handle interface 40 comprises a short tube 70 having an outer diameter that fits closely within the cavity 66 of the shaft member 36. A proximal flange 72 extends outward from the tube 70 and preferably mirrors the shape of the flange 54 on the shaft member 36. More particularly, both flanges 54, 72 have two opposed arcuate edges and two straight edges therebetween so as to have a circular shape with opposed chordal cutouts. An internally threaded bore 74 extends through the tube 70 and opens at its proximal end to receive the threaded boss 46 of the surgical handle 30. Coupling holes 76 are also provided in the flange 72 in the same number and pattern as the coupling holes 64 on the flange 54. In addition an open slot 77 is provided between the coupling holes to facilitate severing a flexible attachment thread (described below).

The valve abutment portion 42, also seen in the plan views of FIGS. 8 and 9, includes a tubular body 80 defining therethrough a central bore 82. An axial slot 84 opens in one side of the bore and is sized to receive the rail 56 of the shaft member 36. A plurality, in this case three, sewing ring brackets 86 extend outward from the tubular body 80. Each bracket 86 has a radially-extending portion 88 with a pair of through holes 90 formed therein and an axially-extending portion 92. The generally right angle combinations of the three radially-extending portions 88 and axially-extending portions 92 contact the sewing ring 24 of the valve 22, with the portions 92 projecting within the annular sewing ring to accurately center the valve 22 in the holder 42. A pair of ears 94 project in a proximal direction from the tubular body 80 on opposite lateral sides of the central bore 82. These ears 94 each include an upper flange (not numbered) that provides structure for retaining a protective assembly 102 including a disk-shaped clip 104 and cage 106 (shown in FIGS. 4A-4B) on the holder 20. The cage 106 snaps on to the clip 104 and provides protection for the valve 22 during storage, transport, and handling in the operating room prior to implantation. The assembly 102 of the clip 104 and cage 106 also provides a means of grasping the complete unit in one hand while deploying the holder with the other hand. In addition the perforated cage 106 can potentially act as a rinsing cage protecting the valve during the operating room rinsing procedure.

Detailed operation of the valve holder 20 of the present invention will now be described with respect to FIGS. 3A-3D, 4A-4B, and 5A-5D.

Figure 5B:
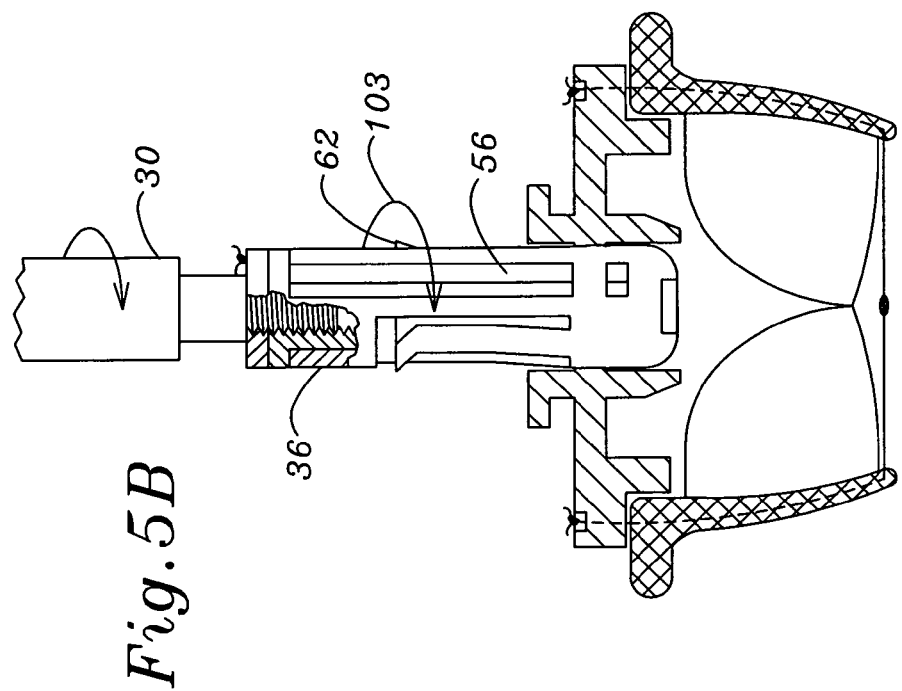
FIGS. 5A and 5B are partial axial sectional views of the holder, handle and valve combination corresponding to the positions of the shaft member shown in FIGS. 3A and 3B.
Figure 5A:
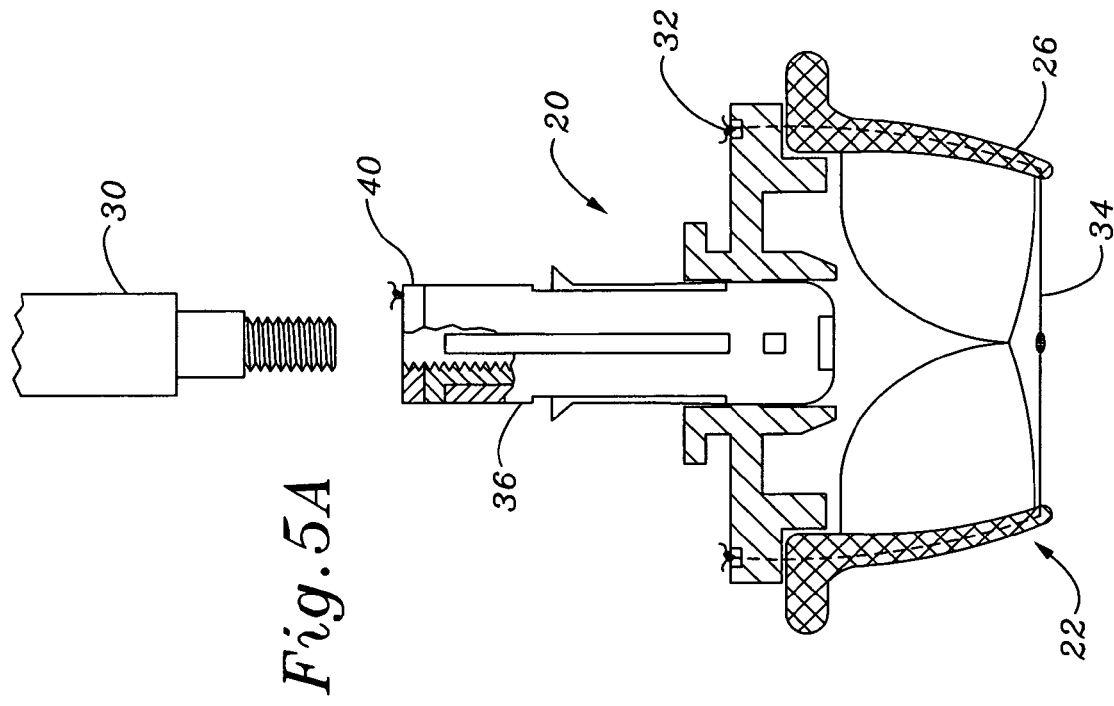

FIGS. 3A, 4A, and 5A illustrate the holder 20 assembled and prior to actuation of the shaft member 36 to constrict the valve commissure posts 26 and move the attachment flexible material to a steep angle. Referring to FIG. 2, in the assembled state of the holder 20, the tubular body 50 of the shaft member 36 fits concentrically within the bore 82 of the valve abutment portion 42, and the tube 70 of the handle interface 40 extends into the bore 66 of the shaft member. The flange 72 of the handle interface 40 matches up with the flange 54 of the shaft member 36, such that the coupling holes 64, 76 line up. FIGS. 3A and 3B show a coupling suture thread 100 initially tied to interface 40 via hole 76a and crossed over slot 77 to hole 76b. The thread 100 extends through aligned holes 76b and 64, and ties off again at hole 76a. The thread 100 can be severed with a scalpel in slot 77. This configuration removably attaches the handle interface 40 to the shaft member 36, and because the handle 30 threads into the bore 74, the handle is removably attached to the shaft member (indeed, the handle is removably attached in two ways to the shaft member, by threading and by the quick release thread). In the position shown in FIG. 3A, the shaft member 36 is constrained axially with respect to the valve abutment portion 42 by interaction of the gap 58 in the rail 56 (see FIG. 2) with an internal shoulder (not numbered) in the valve abutment portion bore 82. The internal shoulder projects into the gap 58 and because the rail 56 extends on either side of the shoulder the shaft member 36 is constrained from moving axially in either direction (but is not entirely constrained from rotational movement).

FIG. 3A best illustrates the attachment of the holder 20 to the heart valve 22 using the lengths of flexible material 32. As mentioned, the lengths of flexible material 32 may be sutures, and they pass through suture-permeable portions of the valve 22, such as through an outer fabric covering. Each length of flexible material 32 extends through the valve 22 and the two holes 90 of the sewing ring bracket 86. More specifically, each length of flexible material 32 is tied at one end to a first sewing ring bracket hole 90 and extends axially through the corresponding commissure post 26 of the valve 22, preferably crossing over as it does. The first segments 34 of the lengths of flexible material 32 extend radially inward from a distal tip of one of the commissure posts 26 to a central location generally along the flow axis of the valve 22, and from there radially outward to a second commissure post. The flexible material 32 then extends axially through the second commissure post 26 and through a hole 90 in a second sewing ring bracket 86, where it is tied off. In the tri-leaflet valve 22 shown, there are three lengths of flexible material 32 that each extend between two of the commissure posts 26, and therefore the first segments 34 are arranged between the distal tips of the commissure posts as shown in FIG. 3A. These three segments 34 are arranged generally in a plane between the commissure posts 26, and though tautly threaded through the valve 22 they do not pull the commissure posts 26 inward to any great degree so that the valve can be in a relaxed state during a potentially long storage period.

FIGS. 4A-4B show a protective transport cage 102 in cross-section coupled to the disk 104. The transport cage 102 comprises a generally circular disk portion 104 and a tubular cage portion 106. The disk portion 104 includes a central opening and a lateral cutout (not shown) enabling it to be coupled to the valve abutment portion 42, and specifically to the ears 94 thereof. The cage portion 106 couples to and extends axially from a periphery of the disk portion 104, and generally surrounds and protects the valve 22 when assembled with the holder 20. Although not shown, the cage portion 106 includes a number of perforations or cutouts so that the valve 22 may be effectively rinsed while the transport cage 102 remains in place. That is, the assembly shown in FIG. 4A minus the attached surgical handle 30 is that which is packaged for storage by the manufacture. The transport cage 102 remains in place during storage, transport, and subsequent deployment. It may also remain in place during rinsing by the surgical staff. The transport cage 102 functions much like the "rinse cage" disclosed in U.S. Pat. No. 6,416, 547, the disclosure of which is expressly incorporated herein by reference.

FIGS. 3B and 5B show the assembled holder 20 after rotation of the shaft member 36 in the clockwise direction of the arrow 103 in FIG. 3B. The handle 30 rotates in the same direction as shown, and is used to turn the shaft member 36 after it has been fully threaded into the handle interface 40. The total extent of rotation is less than 45°. Once rotated, the axial rail 56 on the shaft member 36 lines up with the axial slot 84 in the valve abutment portion 42. The shaft member 36 is thus in a "first position" with respect to the valve abutment portion 42, which is to say that it is retracted in a proximal direction. In the first position the distal tip of the shaft member 36 is located to the inflow side of the valve leaflets 44. The "first position" as used in the appended claims could also refer to the slightly rotated position shown in FIG. 3A, the position being in reference to the relative axial position of the shaft member 36 with respect to the valve abutment portion 42 (or valve 22, for that matter). The reader will note in FIG. 3B that the cantilevered pawl 62 is located proximally with respect to the valve abutment portion 42.

FIGS. 1A-1C show commissure posts 26 pulled inward or constricted radially and the first segments 34 move to a steep angle position by deploying the holder 20. This step should be accomplished prior to threading the loose implant sutures 28 through the sewing ring 24. In the illustrated embodiment, the commissure posts 26 are pulled inward upon distal displacement of the shaft member 36 from a first position to a second position with respect to the valve abutment portion 42. In addition first segments 34 move to a steep angle position.

Figure 3D:
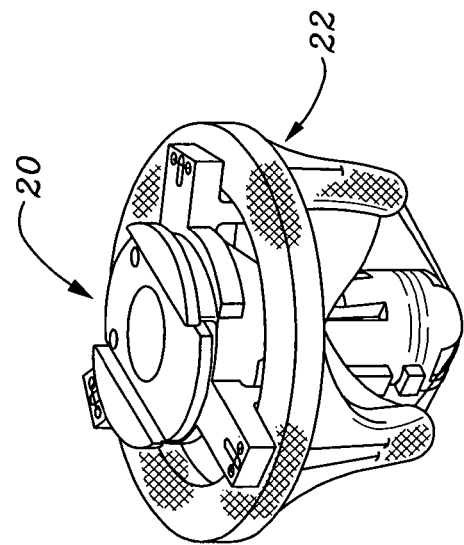
FIG. 3D is a perspective view as in FIG. 3C after removal of the surgical handle and a handle interface to permit greater visibility during the implant procedure.
Figure 3C:
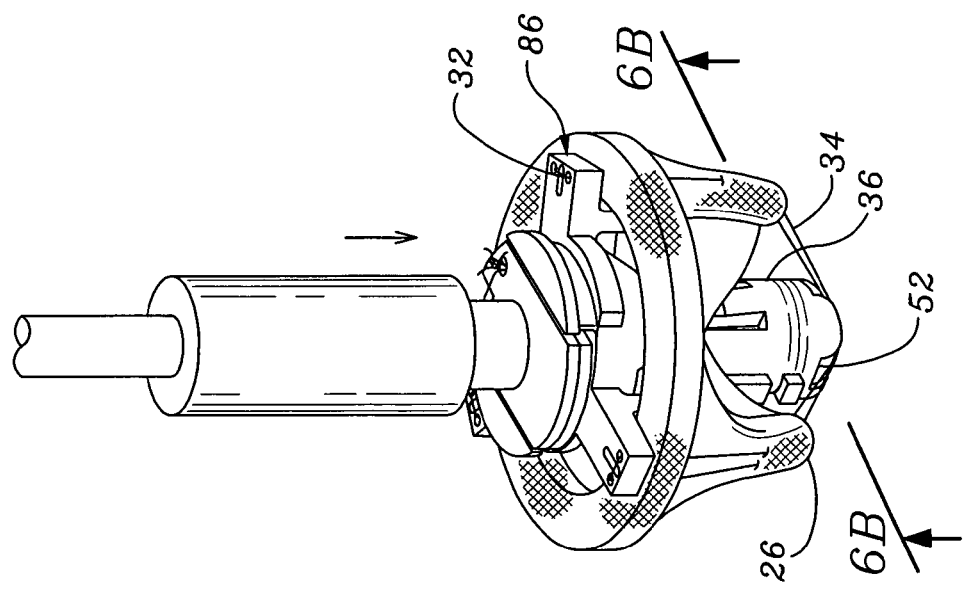
FIG. 3C is a perspective view as in FIG. 3B after axial displacement of the shaft member from a first position to a second position where a distal tip of the shaft member contacts lengths of flexible material that secure the holder to the heart valve.

FIGS. 3C, 4B, and 5C show the shaft member 36 displaced to its second position with the first segments 34 moved to a steep angle position and the commissure posts 26 pulled inward. The shaft member 36 includes the aforementioned notches 52 at its outflow or distal end that engage and capture the first segments 34 of the lengths of flexible material 32. The notches 52 are preferably radially spaced 1200 apart so as to accept and capture the similarly arrayed first segments 34. As the shaft member 36 moves from its proximal, first position to its distal, second position it pushes through the valve leaflets and displaces the first segments 34 in a distal direction creating greater tension in the lengths of flexible material 32, pulling the commissure posts 26 radially inward and moving first segments 34 to a steep angle. After a certain amount of axial travel of the shaft member 36, the pawls 62 spring outward from within the bore 82 of the valve abutment portion 42, as seen in FIG. 5C. The pawls 62 therefore restrain the shaft member 36 in its second position with respect to the valve abutment portion 42. In the second position the distal tip of the shaft member 36 is located to the outflow side of the valve leaflets.

The commissure posts 26 start from a relatively straight orientation seen in FIG. 4A, having a spacing $S_1$ (it will be understood that a true radial cross-section through the center of the valve 22 will not cross two commissure posts 26, and thus the cross-sectional view is in two planes). After movement of the shaft member 36 to its second position, the commissure posts 26 have a spacing $S_2$ seen in FIG. 4B. In a preferred embodiment, the range ratio of the spacing $S_2$ to $S_1$ is about 50 to 60%.

In its second position, the shaft member 36 creates a tent of sorts with the first segments 34, as seen in FIG. 5C. Desirably, the distal tip of the shaft member 36 extends a distance A past the tips of the commissure posts 26, such that the first segments 34 assume an angle a with respect to a radial plane 110. Preferably, the distance A range is about 9 mm, and the angle a is about 40°. This final configuration of the holder 20 just prior to implantation of the valve 22 helps prevent implant suture looping around the commissure posts 26 in three ways. First of all, the commissure posts 26 are pulled inward which reduces their radial profile and thus reduces the likelihood of looping one of the implant sutures around one of the posts. Secondly, the tautly strung first segments 34 extending at an angle α as shown in FIG. 5C together form a conical deflection barrier of sorts guiding the implant sutures around commissure posts 26. Thirdly, the distal tip of the shaft member 36 is relatively broad which fills some of the space between the commissure posts 26 and further helps prevent looping.

FIG. 5C shows detachment of the surgical handle 30 along with the handle interface 40 from the holder 20, while FIG. 3D shows the remaining holder 20 coupled to the valve 22. The ability to quickly release the handle 30 from holder 20 by severing the coupling suture thread 100 is a great advantage to the surgeon after seating the valve 22 in the mitral annulus MA, such as seen in FIG. 1B. After removing the handle 30 with handle interface 40 and thread 100, the surgeon has much greater visibility to tie off the loose implant sutures 28. The shaft member 36 remains in its second position due to engagement of the pawls 62 with the valve abutment portion 42.

Finally, FIG. 5D illustrates removal of the holder 20 from the valve 22 by severance of a mid-portion of each of the lengths of flexible material 32. Because at least one free end of the lengths of flexible material 32 is tied to the valve abutment portion 42, the surgeon can easily pull the holder 20 from engagement with the valve 22. That is, the lengths of flexible material 32, which may be sutures, easily slide through the suture-permeable material of the valve 22. It should be noted that the ears 94 on the valve abutment portion 42 are convenient for use in gripping the holder 20 with forceps or the like.

FIGS. 6A and 6B are plan views of the outflow end of the valve 22 both before and after actuation of the shaft member 36. The first segments 34 of the lengths of flexible material 32 are shown thicker in FIGS. 6A and in the enlarged view of FIG. 7, and illustrate the interaction between them along the flow axis. That is, the three first segments 32 mutually cross over one another so that they meet along the flow axis. Because of this mutual interaction, all three first lengths 32 are located at the proper position for engagement with the shaft member 36. FIG. 6B shows the radially directed notches 52 receiving the three pairs of the first segments 32.

Figure 10:
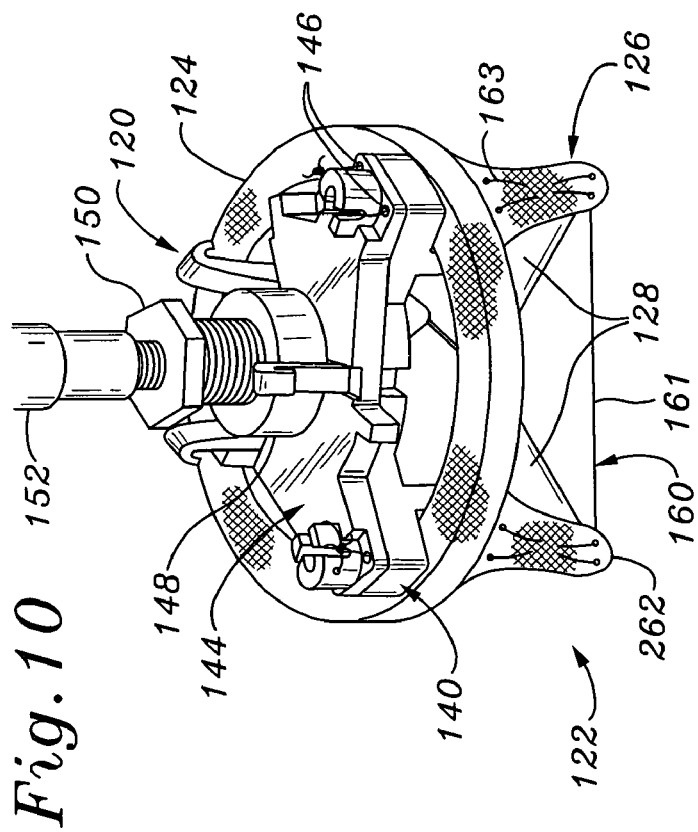
FIG. 10 is a perspective view of a heart valve holder of the present invention assembled to the inflow side of a tissue-type heart valve.

With reference to FIG. 10 an alternative exemplary holder 120 of the present invention is shown attached to a tissue-type heart valve 122. The heart valve 122 includes an annular sewing ring 124 on an inflow side, and a plurality of commissure posts 126 projecting generally axially in the outflow direction. The holder 120 attaches to the sewing ring 124 on the inflow side of the valve 122, which also is the proximal (i.e., accessible) side during implantation. That is, the commissure posts 126 project distally toward the outflow side of the valve 122, defining the leading end of the valve during implantation.

The heart valve 122 further includes a plurality of flexible leaflets 128 that are supported by and extend between the commissure posts 126. The leaflets 128 provide the occluding surfaces of the valve 122, and may be made of individual pieces of bovine pericardium, for example. Alternatively, the leaflets 128 may be part of an entire xenograft, or homograft. In the former instance, natural porcine (pig) valves are particularly useful. Therefore it should be understood that the leaflets 128 may be formed of a variety of materials, none of which is limiting with respect to the present invention. In addition, there are preferably three such leaflets 128 corresponding to three commissure posts 126.

Various constructions for the heart valve 122 are known, which may include metallic or plastic stent elements, a silicone or urethane insert for the sewing ring 124, biocompatible fabric (i.e., polyester) covering around one or more of the elements, etc. In a preferred embodiment, the heart valve 122 includes an internal metallic wireform (not shown) having an undulating shape with a plurality of arcuate cusps connected by upstanding commissures. The wireform commissures provide internal structure for the commissure posts 126 of the valve, and are somewhat flexible so as to be able to flex or cantilever inward. The holder 120 of the present invention facilitates this flexing, though the invention may be practiced in its broadest sense without causing inward movement of the commissure posts. It should be noted that other internal constructions of heart valve 122 having movable commissure posts are available with which the holder 120 of the present invention may function equally as well.

An exemplary holder 120 of the present invention includes a rigid structure of three relatively movable elements. A plate-like valve abutment portion 140 lies against the inflow side of the sewing ring 124 and includes a plurality of through holes around its periphery. A plate-like commissure adjusting portion 144 generally mirrors the shape of the valve abutment portion 140, and also includes a plurality of peripheral through holes 146. The adjusting portion 144 further includes a centrally located and internally threaded boss 148 that projects in a proximal direction from the otherwise generally planar adjusting portion. Finally, an adjusting member 150 having external threads thereon is sized to mate with the internal threads of the boss 148. It should be understood that the function of the holder 120 in constricting the valve commissures may be accomplished with different structures than the one shown.

Figure 11:
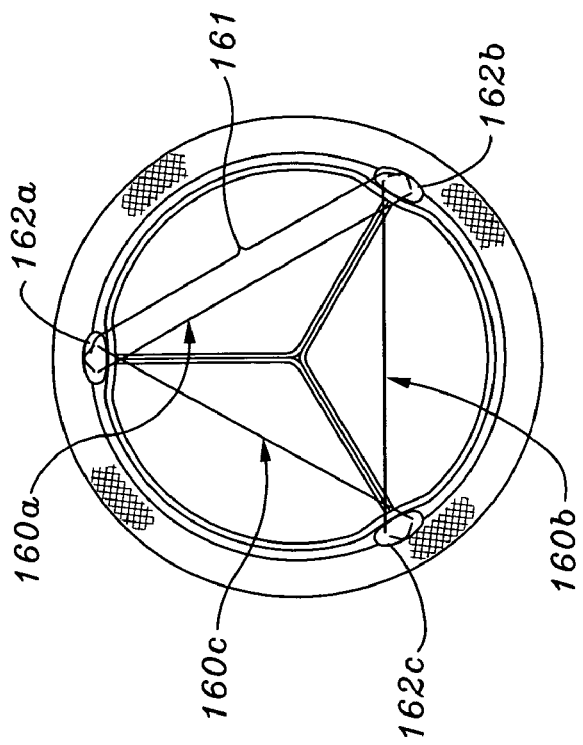
FIG. 11 is a plan view of the outflow end of the valve and holder of FIG. 10.
Figure 12:
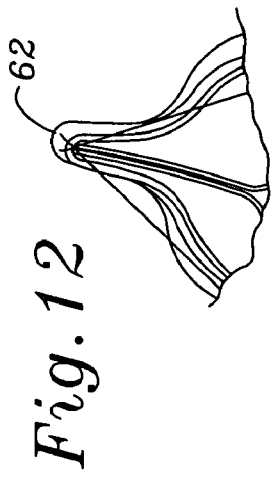
FIG. 12 is a cutaway perspective view of one of the commissures of the valve shown in FIG. 10.

A plurality of lengths of flexible material 160 is shown in FIGS. 10-12 partly extending between the tips 162 of the commissure posts 126. In the preferred embodiment, the lengths of flexible material 160 comprise mono- or polyfilament sutures, and that exemplary nomenclature will be used herein. Because there are three commissure posts 126, there are at least three lengths of sutures 160 extending therebetween in an equilateral triangular configuration. Each length of suture 160 includes a first segment 161 spanning between two of the commissure posts 126. Second segments 163 of each length of suture 160 extend axially in a proximal direction from the tips 162 and along the post 126, the segments passing through the sewing ring 124 and attaching to the holder 120. This is seen best in the perspective view of FIG. 10. Specifically, both second segments 163 pass through the holes in the valve abutment portion 140 and attach to the adjusting portion 144 at discrete attachment points, for example by tying the free ends of each suture. In this manner, each length of suture 160 may be severed close to one of its points of attachment to the adjusting portion 144 and pulled free of the valve 122 along with the holder 120 by virtue of its remaining attachment point. Further specifics of this arrangement can be seen in U.S. Pat. No. 6,409,758, the disclosure of which is expressly incorporated herein by reference.

As mentioned, the abutment portion 140, adjusting portion 144, and adjusting member 150 are relatively movable. That is, the adjusting member 150 is adapted to cause relative axial displacement between the abutment portion 140 and the adjusting portion 144 (preferably by connecting a handle 152 thereto). Because the abutment portion 140 remains against the sewing ring 124, the adjusting portion 144 translates proximally away from the abutment portion, and attached valve 122. Because the lengths of suture 160 attach to the adjusting portion 144, they are also pulled in the proximal direction. Moreover, because the first segment 161 of each length of suture 160 spans between two of the commissure posts 126, proximal movement of the adjusting portion 144 and attached second segments 163 causes radially inward movement of the tips 162, with the commissure posts 126 generally flexing inward from their structural point of attachment within the valve 122 adjacent the sewing ring 124.

It should be clearly understood that the inward flexing of the commissure post tips 162 reduces the chance of suture looping around the tips, but that certain aspects of the present invention reduce suture looping even without tip flexing. That is, the lengths of suture 160 may attach to the rigid structure of a holder that simply abuts the valve, without the relatively moving elements that cause commissure deflection.

With reference to FIGS. 10-12, the arrangement of the discrete lengths of sutures 160 will now be described. There are desirably three equal lengths of suture 160, each secured at its two free ends to the adjusting portion 144. As mentioned, the second segments 163 pass through the aligned holes 146 in the adjusting portion 144 and abutment portion 140, and then through the sewing ring 124 to a first commissure post 126. From there, the second segments 163 continue generally axially to the tips 162 of adjacent commissure posts 126, and the first segment 161 spans obliquely across the outflow side of the valve 122 structurally coupling the two tips. It should be noted that each of the commissure posts 126 desirably has a fabric covering, and the lengths of suture 160 pass at least once through the fabric covering at the tip 162 or along each post 126. For example, FIG. 12 shows the first segments 161 passing below the fabric covering at the tip 162, and FIG. 10 shows the second segments 163 threading at least once through the fabric. This threaded path guides the lengths of suture 160 along their predetermined paths. It is a simple matter to remove the lengths of suture 160 from the valve 122 along with the holder by pulling them free from the fabric cover.

As seen best in FIGS. 11 and 12, the first segment 161 of each length of suture 160 extends from a circumferential side of the respective commissure post tip 162 that is farthest away from the destination tip. That is, three lengths of sutures 160a, 160b, 160c are seen in FIG. 11 extending between three commissure post tips 162a, 162b, 162c, using a clockwise nomenclature. The first segment 161 of the first length of suture 160a extends from a counter-clockwise side of the first commissure post tip 162a to a clockwise side of the second suture post tip 162b. The other two lengths of sutures are arranged accordingly such that each two adjacent lengths of suture cross over (i.e., intersect) just prior to being threaded into (i.e., just radially inward from) the respective commissure post tips 162. This intersection of the sutures 160 defines a plane or slide closely adjacent to each commissure post tip 162. The plane or slide formed by the crossed sutures 160 helps prevent suture looping because a barrier of sorts is provided that guides loose sutures over each post tip 162.

As seen in FIG. 10, the second segment 163 of each length of suture 160 continues axially along the respective commissure posts 126 and may be threaded into and out of the cloth covering thereover. Desirably, a second crossover of the second segments 163 is provided in the commissure posts 126 to insure that each end is secured to the adjusting portion 144 in the proper orientation. As seen in FIG. 10, therefore, the length of suture 160 that is seen extending between the two visible commissure posts 126 extends upward through the valve 122 and holder 120 to emerge from the closest aligned holes 146 (as shown) and be secured in the cutting guide. This dual crossover thus helps a surgeon identify which lengths of sutures 160 extend between which commissure posts 126.

Figure 13:
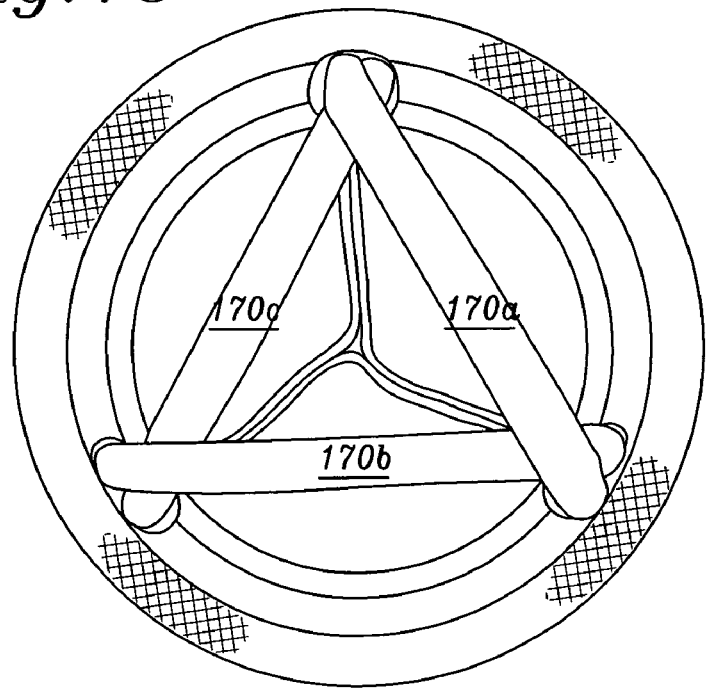
FIGS. 13 and 14 are outflow plan and perspective views, respectively, of an alternative heart valve and holder of present invention.
Figure 14:
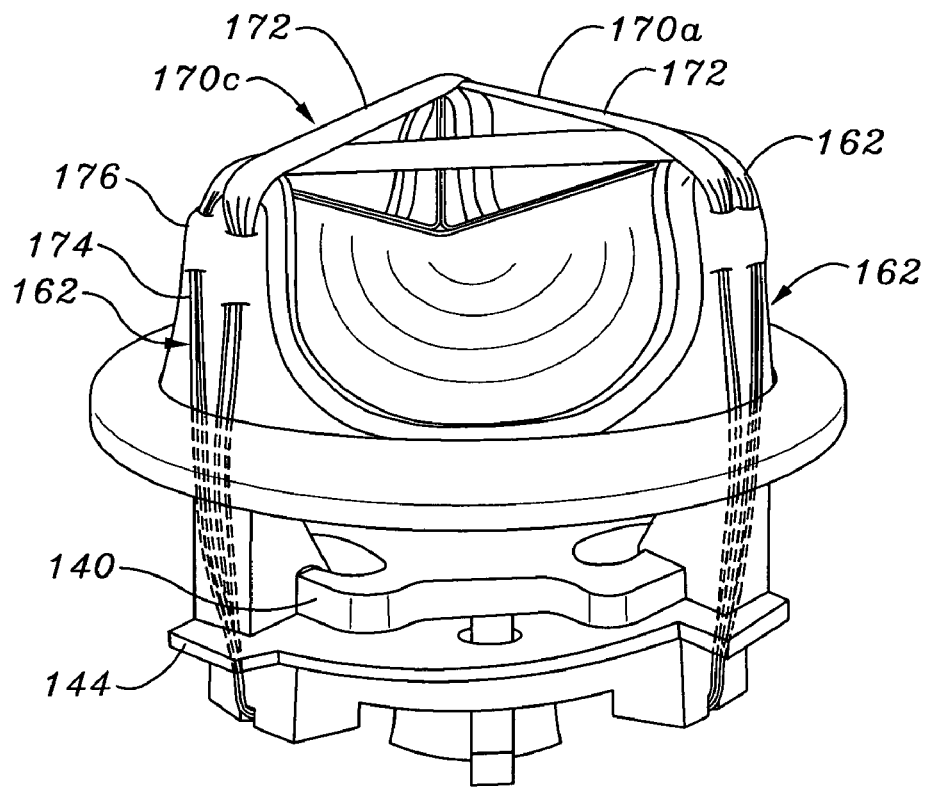

FIGS. 13 and 14 illustrate a second embodiment of heart valve holder of the present invention for preventing suture looping which also provides a planar guard over the commissure tips, similar to the crossed-over lengths of filament-like material of FIGS. 10-12. In general, the holder of FIGS. 13-14 is identical to the holder described above, with the substitution of flexible bands 170a, 170b, 170c instead of lengths of suture 160. The bands 170 may be made of polyester tape, or other suitable biocompatible material similar to sutures. In one embodiment, the bands 170 are substantially wider than they are thick (e.g., formed in a tape or flat strip), and desirably have a width that is approximately equal to the circumferential width of the each of the commissure post tips 162.

As seen best in FIG. 14, first segments 172 of the bands 170 extend between the commissure post tips 162 in a flattened configuration and cross over each adjacent band at or slightly inward from the tip. After extending to the outside of the commissure post tip 162, each band 170 is folded, twisted, or otherwise narrowed into second segments 174 to pass through one or more fabric tunnels 176 along the commissure posts 126. Ultimately, each narrowed second segment 174 passes through aligned holes in the abutment portion 140 and adjusting portion 144 and is secured to the adjusting portion, as described above. The mechanism for the holder 120 of FIGS. 13-14 is similar to that described above in that separation of the abutment portion 140 and adjusting portion 144 pulls the narrowed second segments 174 of the bands 170 to shorten the flattened first segments 172 between the commissure post tips 162. As each second segment 174 is pulled, the first segment 172 follows and is folded or otherwise narrowed as it passes through the fabric cover of the commissure post 126. Moreover, when the holder is removed, one of the second segments 174 of each band 170 is severed close to its point of attachment to the holder and the band 170 may then be pulled free from the valve by virtue of its remaining attachment to the holder. In this regard, the bands 170 may be TEFLON (PTFE) to facilitate sliding through the fabric tunnels in the valve.

Because of the flattened or otherwise planar configuration of the bands 170, suture looping around the commissure post tips 162 is greatly reduced. That is, sutures that contact the bands 170 will be guided over and to the outside of each commissure post tip 162. The bands 170 provide slides of sorts that guide the loose sutures over the commissure post tips 162, and in the preferred embodiment, the bands completely cover the tips to present a smooth, even surface.

Figure 15:
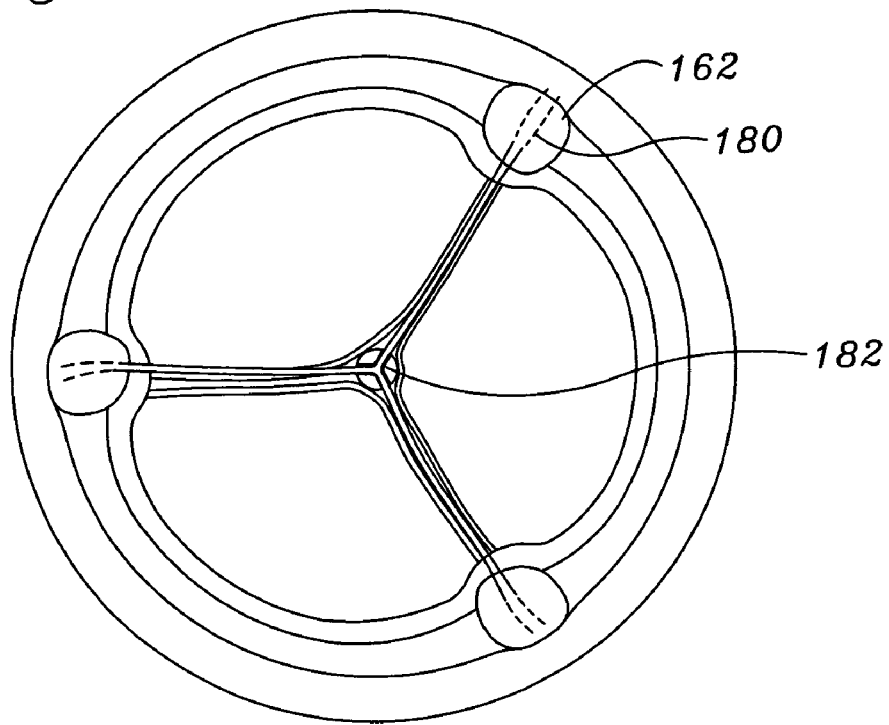
FIGS. 15 and 16 are outflow plan and perspective views, respectively, of a further alternative heart valve and holder of present invention having a central upstanding member.
Figure 16:
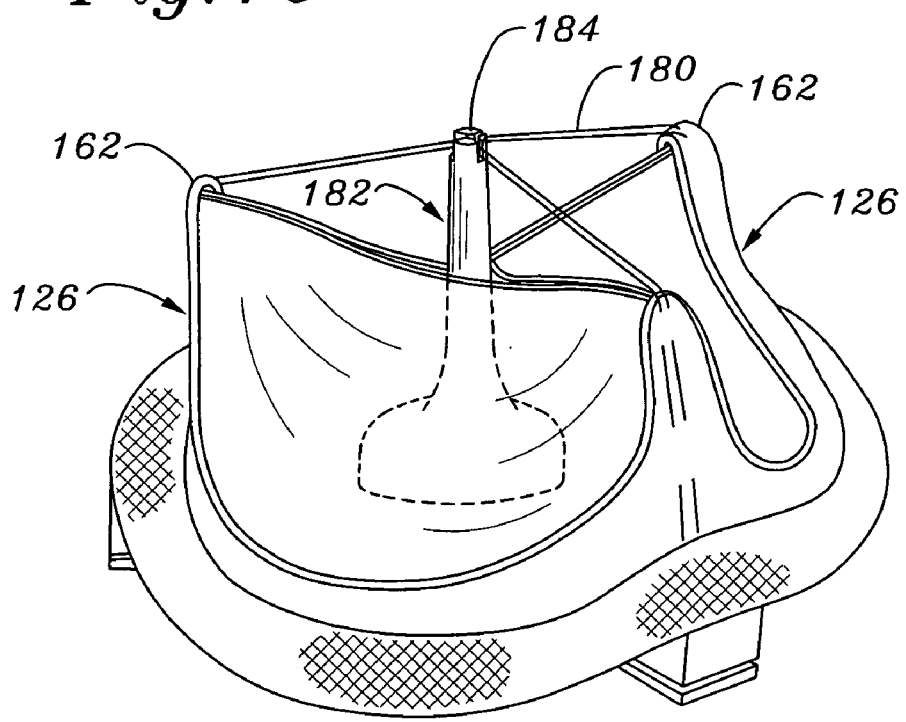

FIGS. 15-17 illustrate a further embodiment of a heart valve holder for preventing suture looping. As seen best in FIG. 16, a plurality of lengths of sutures 180 extends between the commissure post tips 162 across the outflow side of the valve as before, although first to a central upstanding member 182 elevating the lengths of sutures above the commissure post tips. The upstanding member 182 has an upper end 184 with a plurality of grooves or notches therein through which the lengths of suture 180 are threaded. Although the upstanding member 182 is shown as being elevated axially beyond the commissure post tips 162, some of the benefits of reduced suture looping may be realized if the member has the same axial height as the post tips.

Figure 17B:
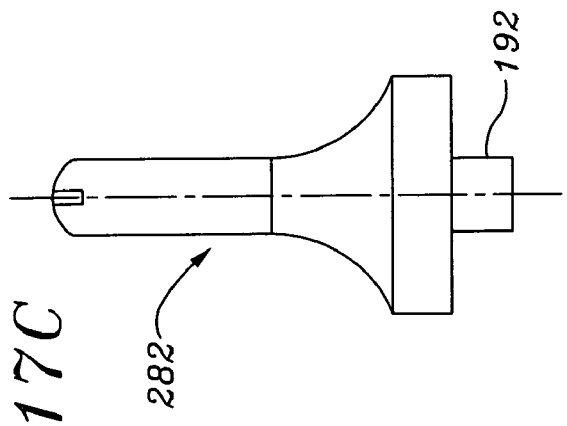
FIGS. 17A-17C are several views of the upstanding member of the holder of FIGS. 15 and 16.
Figure 17C:
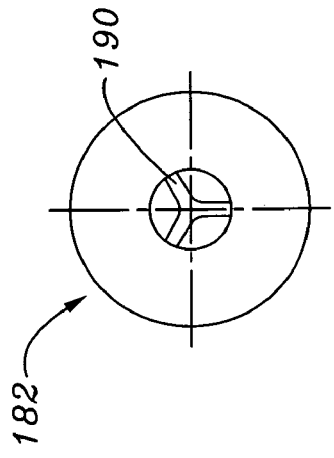
Figure 17A:
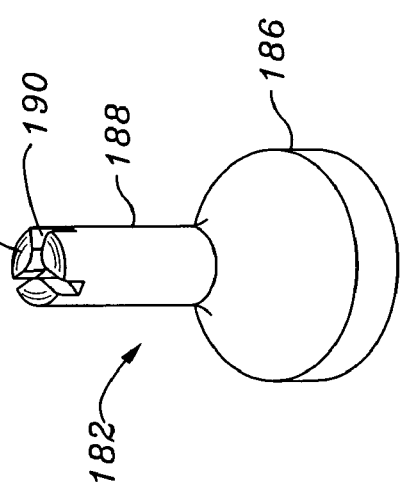

An exemplary embodiment of the upstanding member 182 is illustrated in FIGS. 17A-17C. The member 182 includes a wide base 186 and a narrow shaft 188 terminating in the upper end 184. Three generally radial grooves 190 are formed in the upper end 184 distributed about 120° with respect to each other. These grooves 190 are each aligned with one of the commissure post tips 162 to receive a length of suture 180 extending therefrom. A lower pin 192 in the upstanding member 182 fits within a central bore provided in the center of the abutment portion 140. Alternatively, the upstanding member 182 may be integrally molded with the abutment portion 140. The wide base 186 strengthens the upstanding member 182, and the shaft 188 has a length that projects axially above the commissure posts 126.

As seen in FIG. 16, threading the lengths of suture 180 through the grooves 190 in the upper end 184 of the upstanding member 182 provides a tent of sorts. This suture tent helps to prevent suture looping around the commissure post tip 162. That is, errant sutures that contact any of the angled lengths of suture 180 are guided up and over the nearest commissure post tip 162.

Figure 17D:
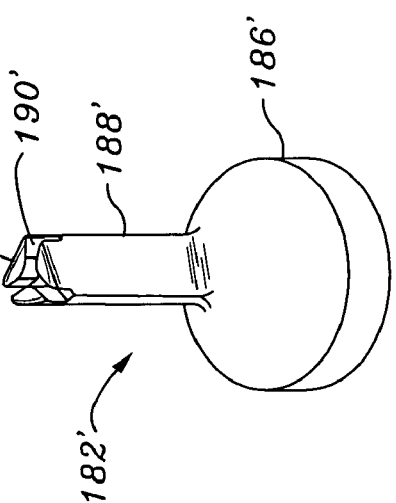
FIG. 17D is a perspective view of an alternative upstanding member of the holder of FIGS. 15 and 16 having a triangular cross-section.

An alternative embodiment of an upstanding member 182' is illustrated in FIG. 17D. As in the earlier embodiment, the member 182' includes a wide base 186' and a narrow shaft 188' terminating in an upper end 184' having three generally radial grooves 190' distributed about 120° with respect to each other. The shaft 188' has a triangular as opposed to circular cross-section so as to better mate with the surrounding leaflets in the assembly of the valve and holder. That is, the three leaflets come together in an equilateral triangle, desirably at the axis of the valve, and the upstanding member 182' will be oriented such that the corners of the triangular shaft 188' project toward each valve commissure, thus bifurcating two leaflets. In this way the midpoint of each leaflet free edge abuts the flat sides of the shaft 188', minimizing any deformation of the leaflet at that midpoint from the extended contact with the shaft 188' during long term storage in a preservative solution.

Figure 18:
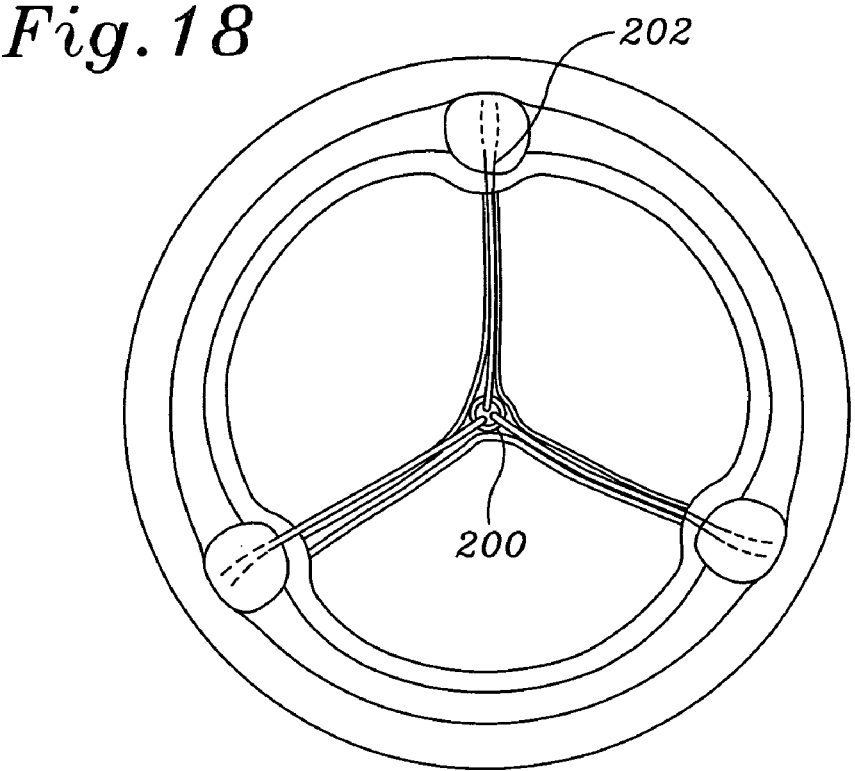
FIGS. 18 and 19 are outflow plan and perspective views, respectively, of a still further alternative heart valve and holder of present invention having a hollow central upstanding member.
Figure 19:
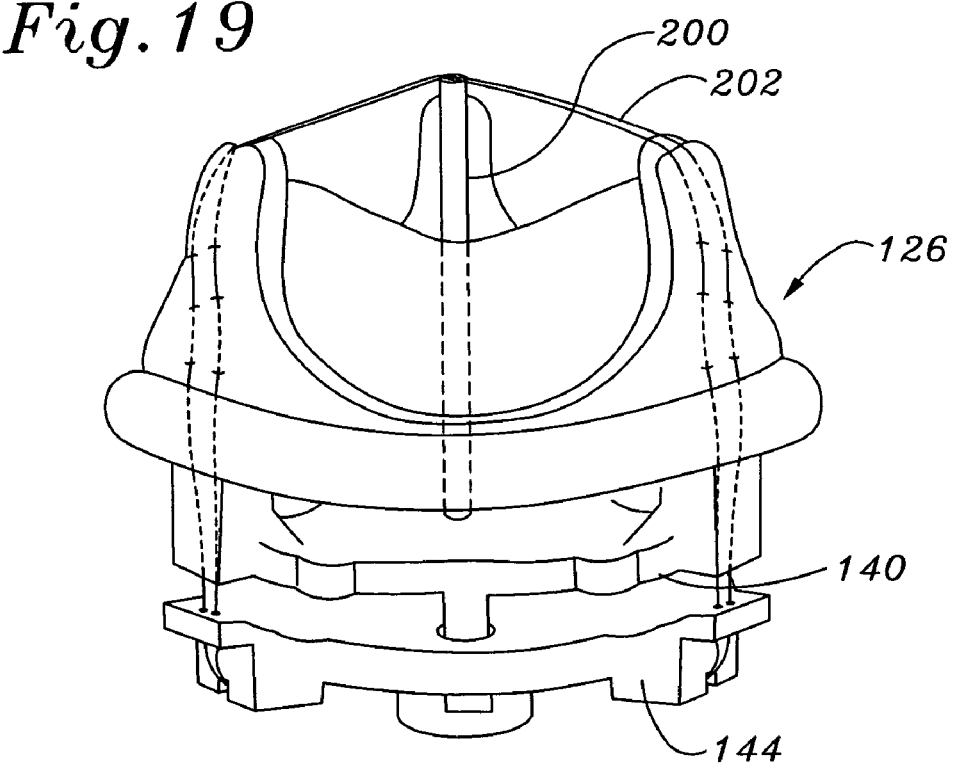

FIGS. 18 and 19 illustrate a further heart valve holder of the present invention that also makes use of a central upstanding member 200, although the member is hollow and the lengths of suture 202 extend axially through the member to be connected to either the abutment portion 140 or adjustment portion 144. The lengths of suture 202 may be filaments or strands, or may be wider bands as described above with respect to FIGS. 13-14. The upstanding member 200 maybe a hollow tubular structure fastened within or molded with the abutment portion 140. Again, the axial height of the upstanding member 200 is greater than the axial height of the commissure posts 126 such that the lengths of suture 202 are tented across the outflow end of the valve.

It will also be appreciated by those of skill in the relevant art that various modifications or changes may be made to the examples and embodiments of the invention described in this provisional application, without departing from the intended spirit and scope of the invention. In this regard, the particular embodiments of the invention described herein are to be understood as examples of the broader inventive concept disclosed in this application.

What is claimed is:

1. A holder for a flexible leaflet prosthetic heart valve that helps prevent suture looping, the heart valve having an inflow end and an outflow end and a flow axis therebetween, the valve including a plurality of generally axially-extending commissure posts circumferentially-spaced around the outflow end that support occluding flexible leaflets of the valve, the holder comprising:
   a valve abutment portion that contacts the inflow end of the valve;
   a member coupled to the valve abutment portion and extending therefrom along the flow axis to a distal tip of the member on the outflow side of the leaflets; and
   a plurality of lengths of flexible material each having first segments angled in the outflow direction from the commissure posts to the distal tip of the member in a tent configuration to help prevent suture looping during implant.

2. The holder of claim 1, wherein each first segment of the lengths of flexible material is angled in the outflow direction about 40° with respect to a radial plane.

3. The holder of claim 1, wherein the member is axially movable relative to the valve abutment portion between a first position wherein the distal tip of the member is located to the inflow side of the leaflets, and a second position wherein the distal tip is located to the outflow side of the leaflets.

4. The holder of claim 1, wherein the valve is of the type that has three leaflets and three commissure posts, and in the first position of the member each first segment extends radially inward and mutually crosses over the other two first segments to retain the point at which they cross over along the flow axis of the valve.

5. The holder of claim 1, wherein the member is solid and includes notches on its distal tip for capturing and retaining midpoints of the first segments of the lengths of flexible material, each first segment angling from one of the commissure posts radially inward to the distal tip of the member and then radially outward to an adjacent commissure post via a notch in the distal tip.

6. The holder of claim 5, wherein each length of flexible material axially extends in second segments along two adjacent commissure posts and attaches to the valve abutment portion at two points such that each length may be severed close to one of its points of attachment to the valve abutment portion and pulled free of the valve along with the valve abutment portion by virtue of its remaining attachment point.

7. The holder of claim 1, further including a generally radially extending clip adapted to removably attach to the valve abutment portion and a generally tubular cage that snaps on to the clip and surrounds the valve to provide protection for the valve during storage, transport, and handling prior to implantation.

8. The holder of claim 7, wherein the cage is perforated to permit rinsing of the valve prior to removal of the cage from the clip.

9. A method for delivering a flexible leaflet prosthetic heart valve and preventing suture looping, comprising:
   providing a flexible leaflet prosthetic heart valve and holder combination, the heart valve having an inflow end and an outflow end and a flow axis therebetween, the valve including a plurality of generally axially-extending commissure posts circumferentially-spaced around the outflow end that support occluding flexible leaflets of the valve, the holder being releasably attached at the inflow end of the valve with a plurality of lengths of flexible material each passing through the valve and having two first segments that each extend radially inward from a commissure post to the flow axis, the holder having a member that is axially movable relative to the valve along the flow axis between a first position and a second position displaced from the first position in the outflow direction, the member having a distal tip; and
   axially displacing the member from the first position to the second position so that the member distal tip passes from the inflow to the outflow side of the flexible leaflets of the valve and engages the first segments of the plurality of lengths of flexible material so that they are angled in the outflow direction from the commissure posts to the distal tip of the member and help prevent suture looping during implant.

10. The method of claim 9, wherein the valve is of the type that has three leaflets and three commissure posts, and in the first position of the member the first segments of each length of flexible material extends radially inward and mutually crosses over the other two first segments to retain the point at which they cross over along the flow axis of the valve, the member including at least one notch on its distal tip and the method including capturing the first segments in the notch when axially displacing the member from the first position to the second position.

11. The method of claim 9, wherein the commissure posts are flexible, the method further including pulling the commissure posts radially inward when axially displacing the member from the first position to the second position.

12. The method of claim 11, wherein the method includes pulling the commissure posts radially inward such that the diameter of a circle defined by tips of the pulled in commissure posts reduces to about 50-60% of a circle defined by the commissure post tips before being pulled inward.

13. The method of claim 9, wherein the holder includes a valve abutment portion that contacts the inflow end of the valve, and the holder includes structure that prevents axial displacement of the member from its first position with respect to the valve abutment portion.

14. The method of claim 13, further including preventing rotation of the member with respect to the valve abutment portion when axially displacing the member from the first position to the second position.

15. The method of claim 9, further including locking the member in its second position.

16. The method of claim 9, wherein the holder includes a valve abutment portion that contacts the inflow end of the valve and a handle interface attached to the valve abutment portion with at least one thread, the handle interface having structure for coupling to a surgical delivery handle, the method including quickly releasing the handle interface and coupled surgical delivery handle from the valve abutment portion by severing the thread.

17. A system for holding a flexible leaflet prosthetic heart valve, the heart valve having an inflow/proximal end and an outflow/distal end and a flow axis therebetween, the valve including a plurality of generally axially-extending commissure posts circumferentially-spaced around the outflow end that support occluding flexible leaflets of the valve, the system comprising:
   a surgical delivery handle having a distal threaded end; and
   a holder comprising a valve abutment portion that contacts the inflow end of the valve, and a handle interface having threading for coupling to the distal threaded end of the surgical delivery handle, the handle interface being coupled to the valve abutment portion with quick release structure to permit quick release of the handle interface and coupled surgical delivery handle from the valve abutment portion without having to unscrew the surgical delivery handle,
   wherein the quick release structure comprises at least one thread coupling the handle interface and the valve abutment portion, wherein the handle interface and coupled surgical delivery handle are released from the valve abutment portion upon severing the thread.

18. A system for holding a flexible leaflet prosthetic heart valve, the heart valve having an inflow/proximal end and an outflow/distal end and a flow axis therebetween, the valve including a plurality of generally axially-extending commissure posts circumferentially-spaced around the outflow end that support occluding flexible leaflets of the valve, the system comprising:
   a surgical delivery handle having a distal threaded end;
   a holder comprising a valve abutment portion that contacts the inflow end of the valve, and a handle interface having threading for coupling to the distal threaded end of the surgical delivery handle, the handle interface being coupled to the valve abutment portion with quick release structure to permit quick release of the handle interface and coupled surgical delivery handle from the valve abutment portion without having to unscrew the surgical delivery handle;
   a plurality of lengths of flexible material secured to the valve abutment portion and passing through the valve to cross over the outflow end of the valve from the commissure posts to a location along the flow axis and help prevent suture looping during implant; and
   a member coupled to the valve abutment portion and extending therefrom along the flow axis to a distal tip on the outflow side of the leaflets, the distal tip engaging the plurality of lengths of flexible material to angle them in the outflow direction from the commissure posts to the distal tip of the member in a tent configuration to help prevent suture looping during implant, wherein the member couples between the valve abutment portion and the handle interface.

19. The system of claim 18, wherein the valve abutment portion comprises a tubular body defining a bore for receiving the member and the member defines a bore for receiving the handle interface.

20. The system of claim 19, wherein the member comprises a generally tubular body and an outwardly extending flange on a proximal end of the body, and the handle interface comprises a generally tubular body and an outwardly extending flange on a proximal end, wherein the handle interface tubular body fits concentrically within the member tubular body and both flanges include coupling holes that align for passage of at least one coupling thread.

21. The system of claim 19, wherein the member is axially movable relative to the valve abutment portion between a first position wherein the distal tip of the member is located to the inflow side of the leaflets, and a second position wherein the distal tip is located to the outflow side of the leaflets.

22. The system of claim 21, wherein the member comprises a generally tubular body having structure for axially restraining the member in the second position with respect to the valve abutment portion.

* * * * *